US009944721B2

(12) United States Patent
Neumann et al.

(10) Patent No.: US 9,944,721 B2
(45) Date of Patent: Apr. 17, 2018

(54) POLYSIALIC ACID AND USE FOR TREATMENT OF NEURODEGENERATIVE AND NEUROINFLAMMATORY DISEASES

(71) Applicants: RHEINISCHE FRIEDRICH-WILHELMS UNIVERSITÄT BONN, Bonn (DE); UNIVERSITÄT ZU KÖLN, Köln (DE)

(72) Inventors: Harald Neumann, Bonn (DE); Jens Kopatz, Bonn (DE); Anahita Shahraz, Bonn (IR); Marcus Karlstetter, Köln (DE); Thomas Langmann, Frechen (DE)

(73) Assignees: RHEINISCHE FRIEDRICH-WILHELMS UNIVERSITÄT BONN, Bonn (DE); UNIVERSITÄT ZU KÖLN, Köln (DE)

( * ) Notice: Subject to any disclaimer, the term of this patent is extended or adjusted under 35 U.S.C. 154(b) by 42 days.

(21) Appl. No.: 14/779,800

(22) PCT Filed: Mar. 18, 2014

(86) PCT No.: PCT/EP2014/055445
§ 371 (c)(1),
(2) Date: Sep. 24, 2015

(87) PCT Pub. No.: WO2014/154537
PCT Pub. Date: Oct. 2, 2014

(65) Prior Publication Data
US 2016/0046734 A1 Feb. 18, 2016

(30) Foreign Application Priority Data
Mar. 28, 2013 (EP) ..................... 13161689

(51) Int. Cl.
A61K 31/715 (2006.01)
C08B 37/00 (2006.01)

(52) U.S. Cl.
CPC ........ C08B 37/0006 (2013.01); A61K 31/715 (2013.01)

(58) Field of Classification Search
None
See application file for complete search history.

(56) References Cited

U.S. PATENT DOCUMENTS 6,395,717 B1    5/2002 Ohta et al.
2013/0324592 A1* 12/2013 Rodriguez Gascon ..................
                                                        A61K 9/0048
                                                        514/44 A

FOREIGN PATENT DOCUMENTS

EP          0502550        9/1992
WO     WO 98/48817    * 11/1998
WO     WO 2010/125110    11/2010
WO     WO 2012/085318 A1 * 6/2012

OTHER PUBLICATIONS

Hollyfield, J.G. et al., Nature Medicine, "Oxidative damage-induced inflammation initiates age-related macular degeneration", Jan. 2008, vol. 14, No. 2, pp. 194-198.*
Shahraz, A. et al. Anti-inflammatory activity of low molecular weight polysialic acid on human macrophages. Sci. Rep. 5, 16800; doi: 10.1038/srep16800 (2015) (Year: 2015).*
H J Jennings, et al, "Determinant specificities of the groups B and C polysaccharides of Neisseria meningitides", Journal of Immunology, vol. 134, No. 4, Apr. 1, 1985, pp. 2651-2657.
Jukka Hayrinen, et al. "High affinity binding of long-chain polysialic acid to antibody, and modulation by divalent cations and polyamines" Molecular Immunology, vol. 39, No. 7-8, Nov. 1, 2002, pp. 399-411.
Evans S V, et al. "Evidence for the extended helical nature of polysaccharide epitopes. The 2.8 A resolution structure and thermodynamics of ligand binding of an antigen binding fragment specific for alpha- (2 fwdarw 8)- polysialic acid", Biochemistry, American Chemical Society, vol. 34, No. 20, Jan. 1, 1995, pp. 6737-6744.
Yasushi Shimoda, et al. "Calcium Ion Binding of Three Different Types of Oligo/Polysialic Acids as studied by equilibrium dialysis and circular dichroic methods" Biochemistry, vol. 33, No. 5, Feb. 1, 1994. pp. 1202-1208.
Y. Wang, et al. "Alleviation of Neurotoxicity by Microglial Human Siglec-11" Journal of Neuroscience, vol. 30, No. 9. Mar. 3, 2010. pp. 3482-3488.
Harvey A. Goldberg, et al. "The Staining of Acidic Proteins on Polyacrylamide Gels: Enhanced Sensitivity and Stability of "Stains-All" Staining in Combination with Silver Nitrate" Analytical Biochemistry, vol. 251, Jan. 27, 1997, pp. 227-233.
Y. Wang "Study of Human-Specific Microglial Receptor Siglec-11 and Generation of Transgenic Mice Expressing Human Siglec-11", PhD Thesis, Faculty of Mathematics and Natural Sciences of the Rheinischen Friedrich-Wilhelms University of Bonn, Mar. 2009.
Ismet Bice, et al. "Downstream processing of high chain length polysialic acid using membrane adsorbers and clay minerals for application in tissue engineering" Eng. Life Sci. vol. 13, No. 2, 2013, pp. 140-148.
International Search Report issued in corresponding International Application No. PCT/EP2014/055445 dated Jun. 2, 2014.

(Continued)

Primary Examiner — Shaojia A Jiang
Assistant Examiner — Bahar Craigo
(74) Attorney, Agent, or Firm — Davidson, Davidson & Kappel, LLC

(57) ABSTRACT

The present invention relates to a branched or unbranched free or glycosidically bound polysialic acid according to general formula (1) as given as follows poly-($\alpha(2\rightarrow8$ or $2\rightarrow9$)Neu5Ac)$_n$ (1) wherein Neu5Ac is N-acetylneuraminic acid, and n is an integer in the range from 14 to 26 and/or pharmaceutically acceptable salts thereof, a polysaccharide composition comprising the polysialic acid (1), and the use as a medicament, particularly in the therapeutic and/or prophylactic treatment of degenerative, demyelinating and inflammatory diseases of the central nervous system, and degenerative or inflammatory retinal diseases.

21 Claims, 14 Drawing Sheets

(56) References Cited

OTHER PUBLICATIONS

Figure 1A:
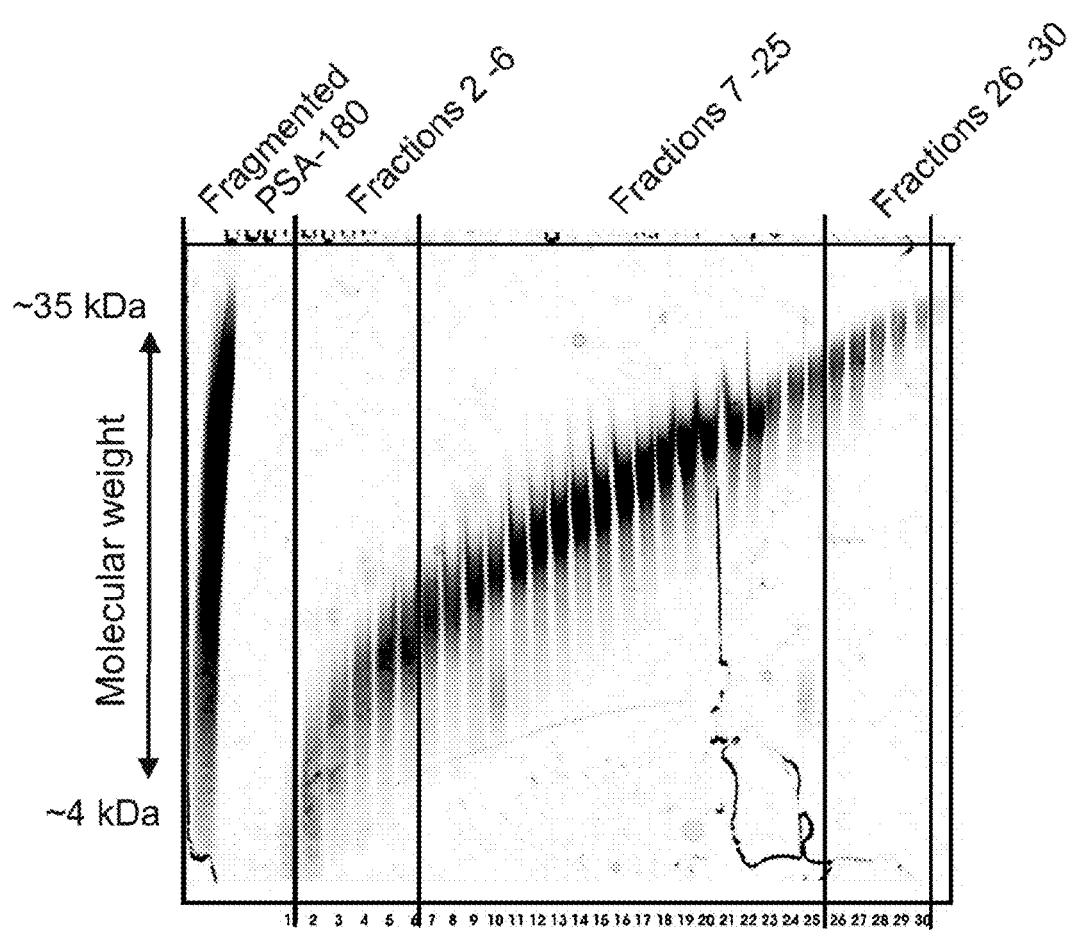

Hultqvist M. et al., "A New Arthritis Therapy With Oxidative Burst Inducers". PLoS Med, vol. 3 Issue 9: e348; pp. 1625-1636 (Sep. 12, 2006).
Ginhoux et al., "Fate Mapping Analysis Reveals That Adult Microglia Derive from Primitive Macrophages" *Science.* 330(6005): pp. 841-845 (Nov. 5, 2010).
Block et al., "Microglia-mediated neurotoxicity: uncovering the molecular mechanisms"; Nature Publishing Group; *Nature Reviews Neuroscience*; vol. 8; pp. 57-69 (Jan. 2007).
Crocker et al., "Siglecs and their roles in the immune system"; Nature Publishing Group: *Nature Reviews Immunology*; vol. 7 pp. 255-266 (Apr. 2007).
Szabo et al., "Quantitative Characterization of a Repeated Acute Joint Inflammation Model in Rats" *Clinical and Experimental Pharmacology and Physiology* 34, pp. 520-526; (2007).
Wirtz et al., "Chemically induced mouse models of intestinal inflammation" Nature Protocols; vol. 2, No. 3 pp. 541-546 (Mar. 15, 2007).
Sundar et al., "Biopolymeric nanoparticles" Sci. Technol. Adv. Mater. vol. 11; pp. 1-13 (2010) doi:10.1088/1468-6996/11/1/014104.
Varki et al., "Multifarious roles of sialic acids in immunity" Ann. N.Y. Acad. Sci. 1253 pp. 16-36 (2012).

* cited by examiner

E

F

G

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
ctgcaccacc aactgcttag                                                 20

<210> SEQ ID NO 2
<211> LENGTH: 20
<212> TYPE: DNA
<213> ORGANISM: Artificial Sequence
<220> FEATURE:
<223> OTHER INFORMATION: reverse primer

<400> SEQUENCE: 2
ttcagctcag ggatgacctt                                                 20

<210> SEQ ID NO 3
<211> LENGTH: 20
<212> TYPE: DNA
<213> ORGANISM: Artificial Sequence
<220> FEATURE:
<223> OTHER INFORMATION: forward primer

<400> SEQUENCE: 3
gacaagcctg tagcccatgt                                                 20

<210> SEQ ID NO 4
<211> LENGTH: 21
<212> TYPE: DNA
<213> ORGANISM: Artificial Sequence
<220> FEATURE:
<223> OTHER INFORMATION: reverse primer

<400> SEQUENCE: 4
aggacctggg agtagatgag g                                               21

<210> SEQ ID NO 5
<211> LENGTH: 21
<212> TYPE: DNA
<213> ORGANISM: Artificial Sequence
<220> FEATURE:
<223> OTHER INFORMATION: forward primer

<400> SEQUENCE: 5
tcttctcatt cctgcttgtg g                                               21

<210> SEQ ID NO 6
<211> LENGTH: 20
<212> TYPE: DNA
<213> ORGANISM: Artificial Sequence
<220> FEATURE:
<223> OTHER INFORMATION: reverse primer

<400> SEQUENCE: 6
agggtctggg ccatagaact                                                 20

<210> SEQ ID NO 7
<211> LENGTH: 20
<212> TYPE: DNA
<213> ORGANISM: Artificial Sequence
```

```
<220> FEATURE:
<223> OTHER INFORMATION: forward primer

<400> SEQUENCE: 7
acaactttgg cattgtggaa                                                    20

<210> SEQ ID NO 8
<211> LENGTH: 20
<212> TYPE: DNA
<213> ORGANISM: Artificial Sequence
<220> FEATURE:
<223> OTHER INFORMATION: reverse primer

<400> SEQUENCE: 8
gatgcaggga tgatgttctg                                                    20

<210> SEQ ID NO 9
<211> LENGTH: 22
<212> TYPE: DNA
<213> ORGANISM: Artificial Sequence
<220> FEATURE:
<223> OTHER INFORMATION: forward primer

<400> SEQUENCE: 9
acaggacagt cctggaaaac ct                                                 22

<210> SEQ ID NO 10
<211> LENGTH: 23
<212> TYPE: DNA
<213> ORGANISM: Artificial Sequence
<220> FEATURE:
<223> OTHER INFORMATION: reverse primer

<400> SEQUENCE: 10
aggcaggaac agaaagcgag cag                                                23
```

POLYSIALIC ACID AND USE FOR TREATMENT OF NEURODEGENERATIVE AND NEUROINFLAMMATORY DISEASES

This application is a U.S. national phase application under 35 U.S.C. § 371 of International Application No. PCT/EP2014/055445, filed Mar. 18, 2014, which claims priority to European Application No. 13 161 689.8, filed Mar. 28, 2013; the disclosures of which are all hereby incorporated by reference herein.

The present invention relates to low weight polysialic acid, a use as a medicament, particularly a use in the treatment of pathological processes of the central nervous system (CNS) and the retina.

A curative therapy of neurodegenerative diseases of the central nervous system (CNS) does not exist and most treatments are therefore symptomatic. This includes several diseases of the CNS and of the retina, which is a specialized part of the CNS. Accordingly to the WHO Classification of Diseases and Related Health Problems (ICD-10) these diseases include degenerative motor neurons diseases (Amyotrophic lateral sclerosis; ICD-10: G12.2), Parkinson's disease (ICD-10: G20), Alzheimer's disease (ICD-10: G30), multiple sclerosis (ICD-10: G35) and degeneration of the macula and posterior pole (senile macular degeneration) (ICD-10: H35.3).

Several data demonstrate that systemic inflammation mediated by pro-inflammatory cytokines released by tissue macrophages is a causal factor sustaining the progression of neurodegeneration in animal models and in human diseases. It was assumed that also microglia might act as transducers of systemic inflammation and effectors of neurodegeneration. It is also known that systemic inflammation triggered by infections can lead to progression of multiple sclerosis and Alzheimer's disease. Likewise, inflammatory processes contribute to the progression of neurodegenerative diseases as Parkinson's disease and amyotrophic lateral sclerosis. Although the primary causes of neurodegenerative diseases are quite diverse, there is strong evidence for a remarkable convergence in the amplification of the neuronal damage by a unique inflammatory profile of microglia. Although it can be surmised that macrophage and microglial pro-inflammatory cytokines, particularly tumor necrosis factor-alpha (TNF-alpha) and reactive oxygen species such as superoxide, act as a driving force of inflammatory tissue and neuronal damage, only limited therapy options are at hand to prevent damage in neurodegenerative diseases. Hence, ongoing local damage in affected tissues is still a major challenge.

Oligosialic and polysialic acid are extended homopolymers of sialic acid. Sialic acid is an N- or O-substituted derivative of neuraminic acid. Polysialic acid (PSA) is found on glycoproteins, and is a component of the capsular polysaccharides of certain pathogenic bacteria. In bacteria, the sialic acid monomers of PSA can be linked by a 2.8 or a 2.9 linkage to form polysialic acid. In human, the sialic acid monomer of PSA is linked by a 2.8 linkage and is acetylated at position 5. The sialic acid monomer N-acetylated at position 5 usually is abbreviated Neu5Ac. At neutral pH, the α(2→8) linkages result in a highly flexible linear molecule, while at low pH the chemical structure of the polymer forms lactones, resulting in a more rigidified structure. The number of monomers in polysialic acid can reach 200, while the average chain length of endogenous PSA chains in *E. coli* K1 have been found to be about 150 to 180 monomers. Most of the PSA chains on the mammalian glycoprotein neural cell adhesion molecule (NCAM) consist of a variable degree of sialic acid monomers. Extended polysialic acid chains have been observed on glycoproteins of human neuroblastoma.

US 2009/0010944 discloses methods of producing an isolated alpha (2→8) or (2→9)oligosialic acid derivative bearing a non-reducing end enriched for one or more de-N-acetyl residues, and methods of use in the detection of *E. coli* K1 and *N. meningitis* bacterial infection, and diagnosing and treating cancer. Further, polysialic acid has been used to improve the pharmacokinetics of proteins. Therefore polysialic acid with a relative high molecular weight between 20 kDa and 40 kDa was attached to recombinant proteins to improve their stability and pharmacokinetics. For example, Xenetic Biosciences PLC, London, UK, marketed a technology using natural polymer polysialic acid to prolong the half-life and improve stability of proteins such as recombinant factor VIII.

Although increasing details of the complex mechanisms of neurodegenerative diseases are identified, it is nearly impossible to predict if a compound may exhibit pro- or anti-inflammatory characteristics. This is the more so, as for example microglia has been implicated as active effector in neurodegenerative diseases, but also may initiate anti-inflammatory effects.

Therefore, the object underlying the present invention was to provide compounds that are usable in the treatment of neurodegenerative and inflammatory diseases.

The problem is solved by a branched or unbranched free or glycosidically bound polysialic acid according to general formula (1) as given as follows and/or pharmaceutically acceptable salts thereof:

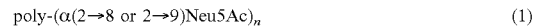
$$\text{poly-}(\alpha(2\rightarrow 8 \text{ or } 2\rightarrow 9)\text{Neu5Ac})_n \quad (1)$$

wherein:
Neu5Ac is N-acetylneuraminic acid, and
n is an integer in the range from 14 to 26.

Furthermore, the invention relates to a pharmaceutical composition comprising the polysialic acid (1) as an active ingredient, and the use as a medicament, particularly in the treatment of degenerative, demyelinating and inflammatory diseases of the central nervous system, and degenerative or inflammatory retinal diseases.

The term "polysialic acid" according to the invention refers to homopolymers of sialic acid comprising more than 10 monomers. Oligosialic acid on the other hand comprises a few monomers typically between 2 to 10 monomers.

Surprisingly it was found that polysialic acid according to general formula (1) can be used for the prevention and/or treatment of pathological processes of the central nervous system (CNS) and the retina. It was found that low molecular weight polysialic acid with a molecular weight between about 4.3 and 8 kDa or a chain length between 14 to 26 monomers, respectively, reduced the production of pro-inflammatory mediators of microglia and tissue macrophages without interfering with the viability of the cells. In contrast, 2.8-linked sialic acids with a length between 2 to 6 monomers showed no effect, while polysialic acid of higher molecular weight (>12 kDa) attenuated the cell viability of the human microglia. Thus, the polysialic acid derivatives (1) are suitable for treating or preventing diseases involving inflammatory microglia or macrophages. It is assumed that the polysialic acid (1) can prevent the microglial or macrophage production of pro-inflammatory cytokines or reactive oxygen species. Without being bound to a special theory, it is assumed that the polysialic acid (1) may bind to a human lineage specific membrane protein named Sialic-acid-binding immunoglobulin-like lectin-11 (Siglec-11) which is expressed on microglia and certain tissue macrophages.

The monosaccharide N-acetylneuraminic acid (Neu5Ac) is denoted 5-acetamido-2,4-dihydroxy-6-(1,2,3-trihydroxy-propyl)oxane-2-carboxylic acid according to the IUPAC nomenclature. The Neu5Ac monomer units of the polysialic acid polysaccharide are joined together by glycosidic bonds. The Neu5Ac monomers can be linked by a (2→8) or a (2→9) linkage to form polysialic acid molecules. The polysialic acid (1) can include monomers that are 2.8-linked, or monomers that are 2.9-linked, or monomers that are 2.8-linked and 2.9-linked, for example in alternate or random order. The polysialic acid (1) can be poly(2.8-linked) or poly(2.9-linked) polysialic acid, preferable a poly(2.8-linked) polysialic acid. Preferably, the Neu5Ac monomers are linked by a α(2→8) linkage. Preferably, the polysialic acid is poly-(α(2→8)Neu5Ac)$_n$ polysialic acid.

In a preferred embodiment, n is an integer in the range from 16 to 24. In a further preferred embodiment, n is an integer in the range from 18 to 20. Advantageously, polysialic acid of such chain length can combine good effects in the treatment of degenerative diseases of the central nervous system and the retina with the potential for not being immediately filtered into the urine by the kidney and with the potential to keep its linear structure without formation of tertiary structures.

The polysialic acid can be a branched or unbranched polymer. The term "unbranched" according to the invention is to be understood as meaning a straight-chain polysialic acid polymer comprising a linear sequence of Neu5Ac monomers. The term "branched" according to the invention is to be understood as meaning a polysialic acid polymer that is composed of a main chain with one or more substituent side chains or branches. Preferably, the polysialic acid is an unbranched polymer. In a preferred embodiment, the polysialic acid forms a linear polymer composed of α(2.8-linked) Neu5Ac monomers. Neu5Ac monomers linked by a 2.8 linkage correspond to the human form of polysialic acid. For use as a medicament, the human form advantageously will provide the most compatible and effective form of polysialic acid. A linear polymer composed of α(2.8-linked) Neu5Ac monomers with a chain length between 14 to 26 monomers results in a highly flexible molecule that is able to provide good binding capacity to its target.

The polysialic acid poly-(α(2→8)Neu5Ac)$_n$ (1) can be free or glycosidically bound. The term "glycosidically bound" according to the invention is to be understood as meaning the polysialic acid that is bound to a further saccharide molecule, or other molecules capable of forming a glycosidic bond such as amino acids. Preferably, the polysialic acid is in the form of the free polysaccharide. The term "free" according to the invention is to be understood as meaning the polysialic acid that is not bound to a further saccharide or other molecule, but is the polysialic acid molecule poly-(α(2→8)Neu5Ac)$_n$ (1) itself.

In further embodiments, the polysialic acid can be glycosidically bound to at least one sugar selected from the group comprising glucose, N-acetylglucosamine, N-acetylgalactosamine, galactose, fucose, mannose and xylose. The term "sugar" according to the invention is to be understood as meaning monosaccharides and disaccharides, which commonly are referred to as sugars. Advantageously, glucose, N-acetylglucosamine, N-acetylgalactosamine, galactose, fucose, mannose and xylose are essential sugars within the human body. The polysialic acid can comprise one terminal sugar molecule or be glycosidically bound to two or more sugar molecules. Further, the polysialic acid or the polysialic acid via a glycosidically bound sugar can glycosidically bind to one or more amino acids to form glycoproteins. Polysialic acid glycosidically linked to one or more sugar molecules or amino acids can result in improved pharmacokinetics. The term "amino acid" according to the invention is to be understood as meaning alpha amino acids, molecules containing both amine and carboxyl functional groups attached to the same carbon, which is called the alpha-carbon. Preferred amino acids are naturally occurring amino acids, selected from the group comprising glycine, alanine, serine, threonine, arginine, lysine, aspartic acid, glutamic acid, asparagine, glutamine, phenylalanine, tyrosine, tryptophan, leucine, valine, isoleucine, cysteine, methionine, histidine and/or proline.

Also suitable are pharmaceutically acceptable salts of the polysialic acid. The term "pharmaceutically acceptable salts" refers to salts prepared from pharmaceutically acceptable non-toxic bases or acids. A corresponding salt can be conveniently prepared from pharmaceutically acceptable non-toxic bases, including inorganic bases and organic bases. Preferred salts derived from inorganic bases include ammonium, calcium, magnesium, potassium and sodium salts. Salts derived from pharmaceutically acceptable organic non-toxic bases include salts of primary, secondary, and tertiary amines, as well as cyclic amines. Preferably, the pharmaceutically acceptable salt is selected from the group comprising sodium, potassium, calcium or magnesium salts.

The polysialic acid of the present invention can be derived from natural or synthetic sources. Methods for the specific synthesis of oligo- and polysaccharides by using the monosaccharide units as precursors are well known by a person skilled in the art. Further, polysialic acid can be derived from a dietary source. Preferably, the oligosialic acid is obtainable from a polysialic acid polymer, for example from bacteria such as *E. coli* K1. The average chain length of endogenous polysialic acid chains in *E. coli* K1 has been found to be about 150 to 180 monomers. Purified polysialic acid produced by *E. coli* is commercially available and can be used for fragmentation, for example by heating the polysialic acid precursor. The reaction mixture can then be purified by standard methods, for example by dialysis followed by separation of the desired fractions comprising polysialic acid fragments using high-performance liquid chromatography.

A further aspect of the present invention relates to a polysaccharide composition comprising a polysialic acid according to general formula (1) as given as follows and/or pharmaceutically acceptable salts thereof: poly-(α(2→8 or 2→9)Neu5Ac)$_n$ (1) wherein Neu5Ac is N-acetylneuraminic acid and n is an integer in the range from 14 to 26, wherein the polysialic acid fragments in the composition have a mean molecular weight between about 4.9 kDa and 7.4 kDa, and ≥90% by weight to ≤100% by weight of the fragments have a molecular weight between about 4.3 kDa and 8 kDa, and ≥0% by weight to ≤5% by weight of the fragments have a molecular weight between 3 kDa and 4.3 kDa, and ≥0% by weight to ≤5% by weight of the fragments have a molecular weight between 8 kDa and 9.5 kDa, wherein the weight-% of the fragments are based on the total weight of the polysialic acid fragments.

Weight percent, weight-% or wt.-% are synonyms that refer to the concentration of a fragment as the weight of the fragment divided by the total weight of the fragments multiplied by 100. The weight-% (wt.-%) of the fragments are calculated based on the total weight amount of the fragments, if not otherwise stated. The total amount of all fragments of the composition does not exceed 100 wt.-%.

The term "mean molecular weight" of polysialic acid is understood in this application to mean the molecular weight average of the polysialic acid fragments as determined by polyacrylamide gel electrophoresis. The molecular weight of the polysialic acid fragments can be detected in comparison with standards of defined molecular weight as described in this application. The number of monomers of polysialic acid can be determined for example by anion-exchange high-performance liquid chromatography (HPLC).

Generally, the chain length of a polymer can be given in monomer units, as molecular weight, or both. Referring to the polysialic acid polysaccharide, a molecular weight between about 4.3 kDa and 8 kDa corresponds to a chain length of n=14 monomers to n=26 monomers, while a molecular weight between about 4.9 kDa and 7.4 kDa corresponds to a chain length of n=16 monomers to n=24 monomers.

In such a polysaccharide composition comprising the polysialic acid (1), the highest point of molecular weight can be about 5 kDa to 6.5 kDa.

The polysialic acid (1) can be poly(2.8-linked) or poly(2.9-linked) polysialic acid, preferable a poly(2.8-linked) polysialic acid. Preferably, the Neu5Ac monomers are linked by a α(2→8) linkage. Preferably, the polysialic acid is poly-(α(2→8)Neu5Ac)$_n$ polysialic acid. In a preferred embodiment, n is an integer in the range from 16 to 24. In a further preferred embodiment, n is an integer in the range from 18 to 20. Preferably, the polysialic acid is an unbranched polymer. In a preferred embodiment, the polysialic acid forms a linear polymer composed of α(2.8-linked) Neu5Ac monomers. Preferably, the polysialic acid is in the form of the free polysaccharide. In further embodiments, the polysialic acid can be glycosidically bound to at least one sugar selected from the group comprising glucose, N-acetylglucosamine, N-acetylgalactosamine, galactose, fucose, mannose and xylose. Further, the polysialic acid or the polysialic acid via a glycosidically bound sugar can glycosidically bind to one or more amino acids to form glycoproteins.

A further aspect of the present invention relates to a branched or unbranched free or glycosidically bound polysialic acid according to general formula (1) as given as follows and/or pharmaceutically acceptable salts thereof:

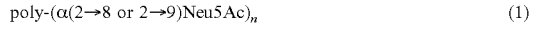

$$\text{poly-}(\alpha(2\rightarrow 8 \text{ or } 2\rightarrow 9)\text{Neu5Ac})_n \qquad (1)$$

wherein:
Neu5Ac is N-acetylneuraminic acid, and
n is an integer in the range from 14 to 26, or the polysaccharide composition comprising the polysialic acid (1), wherein the polysialic acid fragments have a mean molecular weight between about 4.9 kDa and 7.4 kDa, and ≥90% by weight to ≤100% by weight of the fragments have a molecular weight between about 4.3 kDa and 8 kDa, and ≥0% by weight to ≤5% by weight of the fragments have a molecular weight between 3 kDa and 4.3 kDa, and ≥0% by weight to ≤5% by weight of the fragments have a molecular weight between 8 kDa and 9.5 kDa, wherein the weight-% of the fragments are based on the total weight of the polysialic acid fragments, for use as a medicament.

The polysialic acid according to general formula (1) is able to prevent microglial or macrophage production of pro-inflammatory cytokines and reactive oxygen species and thus represents a promising compound for the prevention and/or treatment of pathological processes of the CNS and the retina.

Particularly, the present invention relates to a branched or unbranched free or glycosidically bound polysialic acid according to general formula (1) as given as follows and/or pharmaceutically acceptable salts thereof:

$$\text{poly-}(\alpha(2\rightarrow 8 \text{ or } 2\rightarrow 9)\text{Neu5Ac})_n \qquad (1)$$

wherein:
Neu5Ac is N-acetylneuraminic acid, and
n is an integer in the range from 14 to 26, or the polysaccharide composition comprising the polysialic acid (1) wherein the polysialic acid fragments have a mean molecular weight between about 4.9 kDa and 7.4 kDa, and ≥90% by weight to ≤100% by weight of the fragments have a molecular weight between about 4.3 kDa and 8 kDa, and ≥0% by weight to ≤5% by weight of the fragments have a molecular weight between 3 kDa and 4.3 kDa, and ≥0% by weight to ≤5% by weight of the fragments have a molecular weight between 8 kDa and 9.5 kDa, wherein the weight-% of the fragments are based on the total weight of the polysialic acid fragments, for use in the therapeutic and/or prophylactic treatment of a disease selected from the group comprising degenerative, demyelinating and inflammatory diseases of the central nervous system, and degenerative or inflammatory retinal diseases.

The term "prophylactic treatment" refers to either preventing or inhibiting the development of a clinical condition or disorder or delaying the onset of a pre-clinically evident stage of a clinical condition or disorder. The term "prophylactic treatment" according to the invention is to be understood as meaning that the polysialic acid can be applied before symptoms of the diseases are manifest. Especially, the term "prophylactic treatment" is to be understood as meaning a medical treatment. It can be preferred to use the compounds according to the invention in a prophylactic treatment.

Surprisingly it was found that the polysialic acid (1) and polysaccharide composition comprising the polysialic acid (1), respectively, can be effective in a microglial anti-inflammatory therapy. Particularly, the polysialic acid (1) showed to be effective in preventing retinal microglial activation in an animal model of macula degeneration. Thus, the polysialic acid (1) provides a novel approach to the therapeutic and prophylactic treatment of degenerative or inflammatory retinal diseases.

A further particular advantage of the polysialic acid according to the invention is that the polysialic acid (1) showed to be effective in preventing disease symptoms in an animal model of multiple sclerosis. Particularly, as to date there is no satisfactory therapy to prevent the loss of synapses, axons or neurons, the polysialic acid (1) provides a new and much desired possible use in the treatment of degenerative, demyelinating and inflammatory diseases of the central nervous system.

It is assumed that the degenerative, demyelinating and inflammatory diseases of the central nervous system and degenerative or inflammatory retinal diseases are associated with microglia or tissue macrophage production of TNF-alpha or microglial production of reactive oxygen species, which the polysialic acid (1) can prevent. Without being bound to a special theory, it is assumed that the diseases may be associated with microglia or tissue macrophages expressing Siglec-11.

In a preferred embodiment, the neurodegenerative disease is selected from the group comprising amyotrophic lateral sclerosis, Alzheimer's disease, mild cognitive impairment, dementia with Lewy bodies, Parkinson's disease, and parasomnia. The term "amyotrophic lateral sclerosis" (ICD-10: G12.2) according to the invention is to be understood as meaning a progressive degenerative and inflammatory motor neuron disease with poor prognosis. The term "Parkinson's disease" (ICD-10: G20) refers to a progressive neurodegenerative disease mainly affecting the dopaminergic neurons leading to extrapyramidal and movement disorders. The term "parasomnia" (ICD-10: F51.3/F51.4) according to the invention is to be understood as meaning a sleep disorders that involve abnormal and unnatural movements, behaviors, emotions, perceptions, and dreams during sleep that frequently occurs as prodromal signs of Parkinson's disease. The term "Alzheimer's disease" (ICD-10: G30) according to the invention refers to a degenerative disease of the central nervous system associated with extracellular amyloid-beta plaques and intracellular neurofibrillary tangles composed of hyperphosphorylated tau. The term "mild cognitive impairment" (ICD-10: G31.84) refers to a cognitive impairment often associated with memory loss and frequently seen as prodromal stage of Alzheimer's disease. The term "dementia with Lewy bodies" (ICD-10: G31.8) refers to a type of dementia closely associated with both Alzheimer's and Parkinson's diseases.

It could be shown that the polysialic acid (1) was effective in preventing neurotoxicity in a co-culture system of human neurons and human microglia. Furthermore, it could be shown that the polysialic acid (1) prevented the release of superoxide in human microglia that was induced by the Alzheimer's disease associated amyloid-beta. It could further be shown that the polysialic acid (1) prevented phagocytosis and production of reactive oxygen species of human microglia and prevented damage to neurons in a human microglia-neuron co-culture model of Parkinson's disease.

In a preferred embodiment, the inflammatory disease of the central nervous system is selected from the group comprising septic encephalopathy, severe sepsis with mental involvement or septic episodes associated with neurodegenerative diseases, often associated with progression of Alzheimer's disease.

The term "septic encephalopathy" or "severe sepsis" or "septic episodes" according to the invention is to be understood as a systemic inflammatory reaction of the body induced by a microbial infection or microbial toxins (ICD-10: R65). Severe sepsis is often associated with an encephalopathy that can lead to delirium and permanent cognitive deficits. It could be shown that the polysialic acid (1) was effective in preventing the pro-inflammatory response induced by a chronic sepsis-like status through repeated application of the bacterial toxin lipopolysaccharide.

In a preferred embodiment, the degenerative or inflammatory retinal disease is selected from the group comprising age-related macula degeneration, retinal degeneration including inherited retinal diseases, uveitis, and diabetic retinopathy. The term "senile" or "age-related macular degeneration" according to the invention is to be understood as meaning an atrophic or exudative (ICD-10: H35.3) disease of the retina with degeneration of the macula and posterior pole often associated with Drusen. Age-related macular degeneration is a degenerative disease of the macula, a specialized part of the retina required for colour and sharp vision. This disease involves activated microglia. Furthermore, neovascular vessels show increased leakage and atrophic retinal pigment epithelium associated with Drusen deposits. Age-related macular degeneration leads to a significant loss of retinal neurons and therefore is a major cause of legal blindness. Advantageously, the polysialic acid (1) showed to be particularly effective in preventing retinal microglial activation and inflammation associated vascular leakage in an animal model of macular degeneration. The term "uveitis" according to the invention is to be understood as meaning "autoimmune uveitis" (ICD-10: H20) a chronic inflammation of the uvea caused by a hyper-reactivity of the immune system, which can affect any part of the uveal tract and the retina. The term "diabetic retinopathy" (ICD-10: H36) according to the invention is to be understood as diabetic and inflammatory microvascular changes of the retina leading to retinal damage.

A preferred demyelinating disease of the central nervous system is multiple sclerosis. The term "multiple sclerosis" (ICD-10: G35) according to the invention is to be understood as meaning a demyelinating disease of the central nervous system triggered by an autoimmune attack directed against myelin proteins and finally leading to axonal degeneration and loss of neurons. The term "Devic's disease" (ICD-10: G36.0) according to the invention is to be understood as meaning a demyelinating disease of the optical nerve and spinal cord triggered by an autoimmune attack directed against glial antigens and finally leading to axonal degeneration and loss of neurons. Hence, multiple sclerosis and Devic's disease also can be regarded as a demyelinating disease of the central nervous system. Advantageously, the polysialic acid (1) showed to be effective in improving the clinical symptoms in an animal model of multiple sclerosis.

The polysialic acid (1) can be poly(2.8-linked) or poly (2.9-linked) polysialic acid, preferable a poly(2.8-linked) polysialic acid. Preferably, the Neu5Ac monomers are linked by a $\alpha(2\rightarrow8)$ linkage. Preferably, the polysialic acid is poly-$(\alpha(2\rightarrow8)$Neu5Ac$)_n$ polysialic acid. In a preferred embodiment, n is an integer in the range from 16 to 24. In a further preferred embodiment, n is an integer in the range from 18 to 20. Preferably, the polysialic acid is an unbranched polymer. In a preferred embodiment, the polysialic acid forms a linear polymer composed of $\alpha(2.8$-linked) Neu5Ac monomers. Preferably, the polysialic acid is in the form of the free polysaccharide. In further embodiments, the polysialic acid can be glycosidically bound to at least one sugar selected from the group comprising glucose, N-acetylglucosamine, N-acetylgalactosamine, galactose, fucose, mannose and xylose. Further, the polysialic acid or the polysialic acid via a glycosidically bound sugar can glycosidically bind to one or more amino acids to form glycoproteins.

It could be shown that the polysialic acid (1) showed no neurotoxicity in cultured human neurons. Advantageously, the polysialic acid (1) is able to pass the blood-brain barrier and reach the parenchyma of the central nervous system after systemic application. Thus, the polysialic acid (1) exhibits suitable pharmacokinetics and pharmacotoxicology for a use in the therapy of neurodegenerative diseases.

A further aspect of the present invention relates to a pharmaceutical composition comprising as an active ingredient a polysialic acid (1) or the polysaccharide composition comprising the polysialic acid (1) according to the invention, and a pharmaceutically acceptable carrier. The pharmaceutical composition particularly is usable in the therapeutic and/or prophylactic treatment of a disease selected from the group comprising degenerative, demyelinating and inflammatory diseases of the central nervous system, and degenerative or inflammatory retinal diseases.

The pharmaceutical carrier can be, for example, a solid, liquid, or gas. Suitable carriers and adjuvants can be solid or liquid and correspond to the substances ordinarily employed in formulation technology for pharmaceutical formulations. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. The pharmaceutical compositions may be conveniently presented in unit dosage form and prepared under sterile conditions using standard pharmaceutical techniques well known in the art of pharmacy.

The pharmaceutical composition can be suitable for oral, dermal, rectal, topical, and parenteral administration. Preferably, the pharmaceutical composition is applied via the parenteral, oral or rectal route, as local skin or eye application. Parenteral administration particularly includes intravitreal injection, subcutaneous injection, intravenous injection or perfusion. Pharmaceutical compositions suitable for injectable use or perfusion include sterile aqueous solutions or dispersions. Further, a preservative can be included to prevent the growth of microorganisms.

In a preferred embodiment, the pharmaceutical composition is formulated as a sterile, injectable solution for parenteral administration. Preferably the pharmaceutical composition is administered as an intravitreal injection, subcutaneous injection, intravenous injection or perfusion.

The present invention also relates to the use of a branched or unbranched free or glycosidically bound polysialic acid according to general formula (1) as given as follows and/or pharmaceutically acceptable salts thereof:

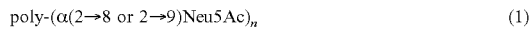
poly-(α(2→8 or 2→9)Neu5Ac)$_n$ (1)

wherein:
NeuSAc is N-acetylneuraminic acid, and
n is an integer in the range from 14 to 26,
or a polysaccharide composition comprising the polysialic acid (1), wherein the polysialic acid fragments have a mean molecular weight between about 4.9 kDa and 7.4 kDa, and ≥90% by weight to ≤100% by weight of the fragments have a molecular weight between about 4.3 kDa and 8 kDa, and ≥0% by weight to ≤5% by weight of the fragments have a molecular weight between 3 kDa and 4.3 kDa, and ≥0% by weight to ≤5% by weight of the fragments have a molecular weight between 8 kDa and 9.5 kDa, wherein the weight-% of the fragments are based on the total weight of the polysialic acid fragments, for the manufacture of a medicament.

The present invention particularly relates to the use of a branched or unbranched free or glycosidically bound polysialic acid according to general formula (1) as given as follows and/or pharmaceutically acceptable salts thereof:

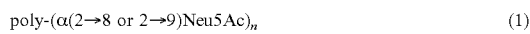
poly-(α(2→8 or 2→9)Neu5Ac)$_n$ (1)

wherein:
Neu5Ac is N-acetylneuraminic acid, and
n is an integer in the range from 14 to 26,
or a polysaccharide composition comprising the polysialic acid (1), wherein the polysialic acid fragments have a mean molecular weight between about 4.9 kDa and 7.4 kDa, and ≤90% by weight to ≤100% by weight of the fragments have a molecular weight between about 4.3 kDa and 8 kDa, and ≥0% by weight to ≤5% by weight of the fragments have a molecular weight between 3 kDa and 4.3 kDa, and ≥0% by weight to ≤5% by weight of the fragments have a molecular weight between 8 kDa and 9.5 kDa, wherein the weight-% of the fragments are based on the total weight of the polysialic acid fragments, for the manufacture of a medicament for the therapeutic and/or prophylactic treatment of a disease selected from the group comprising degenerative, demyelinating and inflammatory diseases of the central nervous system, and degenerative or inflammatory retinal diseases.

A further aspect of the present invention relates to a method of treating a disease selected from the group comprising degenerative, demyelinating or inflammatory disease of the central nervous system, and degenerative or inflammatory retinal diseases, the method comprising administering to a subject in need of a therapeutically effective amount of a branched or unbranched free or glycosidically bound polysialic acid according to general formula (1) as given as follows and/or pharmaceutically acceptable salts thereof:

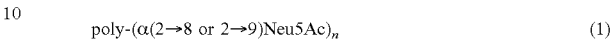
poly-(α(2→8 or 2→9)Neu5Ac)$_n$ (1)

wherein:
Neu5Ac is N-acetylneuraminic acid, and
n is an integer in the range from 14 to 26,
or a polysaccharide composition comprising the polysialic acid (1), wherein the polysialic acid fragments have a mean molecular weight between about 4.9 kDa and 7.4 kDa, and ≥90% by weight to ≤100% by weight of the fragments have a molecular weight between about 4.3 kDa and 8 kDa, and ≥0% by weight to ≤5% by weight of the fragments have a molecular weight between 3 kDa and 4.3 kDa, and ≥0% by weight to ≤5% by weight of the fragments have a molecular weight between 8 kDa and 9.5 kDa, wherein the weight-% of the fragments are based on the total weight of the polysialic acid fragments.

The term "therapeutically effective amount" is used herein to mean an amount or dose sufficient to cause an improvement in a clinically significant condition in the subject.

Unless otherwise defined, the technical and scientific terms used herein have the same meaning as commonly understood by one of ordinary skill in the art to which this invention belongs.

The Examples which follow serve to illustrate the invention in more detail but do not constitute a limitation thereof.

Figure 1B:
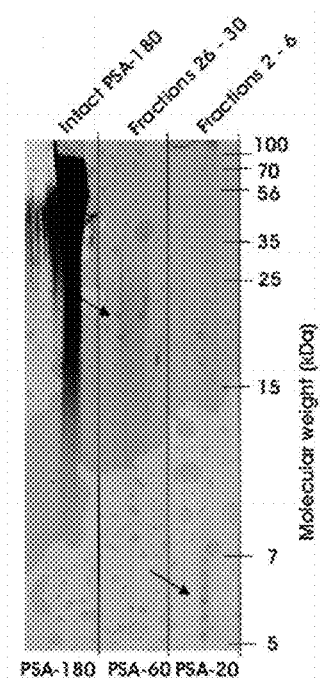

The figures show:

FIG. 1 the characterization of polysialic acid (PSA) fragments. FIG. 1A shows a polyacrylamide gel of the educt PSA-180 after heat-treated fragmentation depicting the different fractions after preparative HPLC, and FIG. 1B shows polyacrylamide gel electrophoresis of the educt PSA-180 and the pooled fractions 2 to 6 (PSA-20) and 26 to 30 (PSA-60).

Figure 2A:
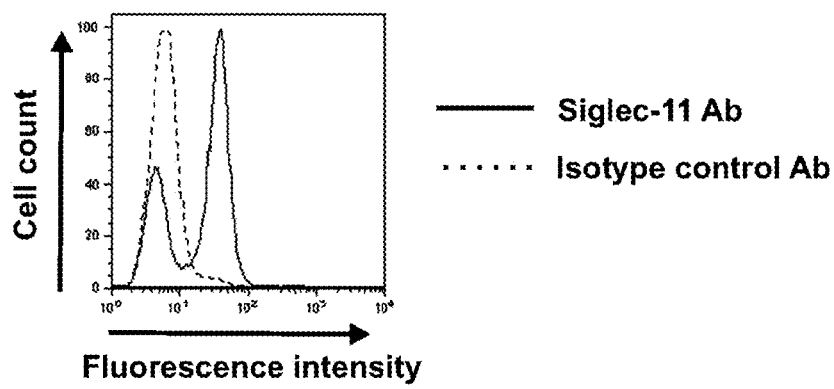
Figure 2B:
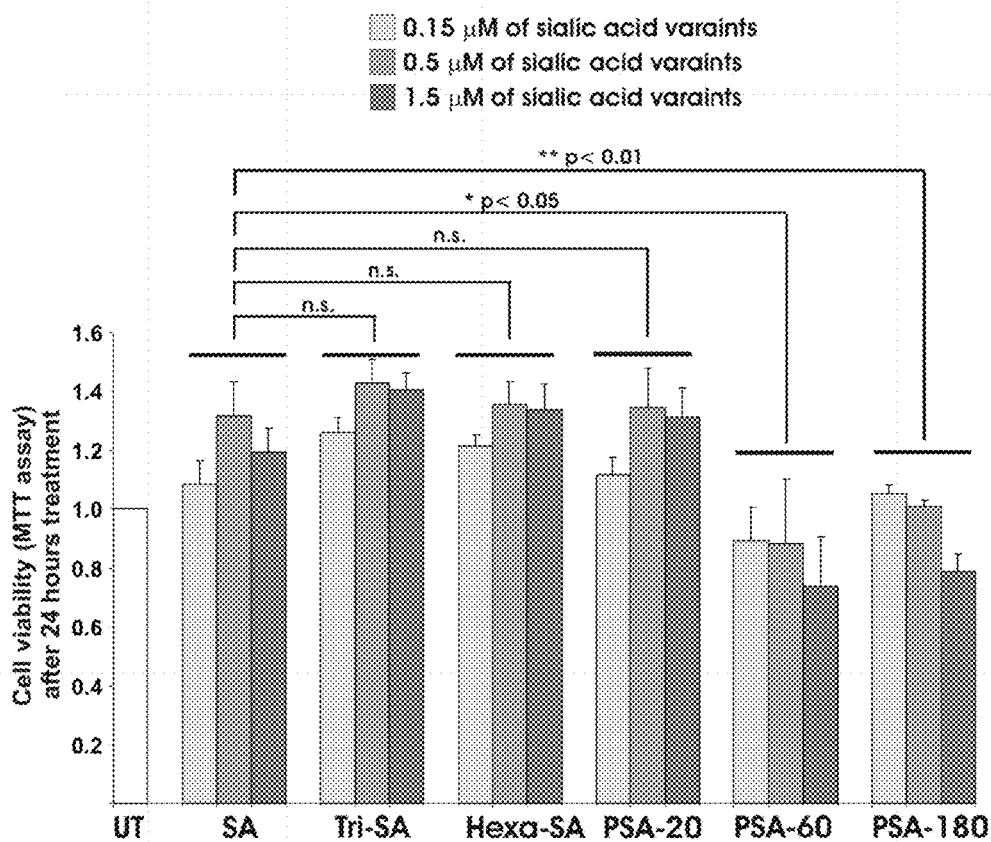

FIG. 2 the results of the determination of toxicity of low molecular weight PSA-20 on human microglia expressing Siglec-11. FIG. 2A shows the cell surface expression of Siglec-11 (Siglec-11 Ab) on the human microglial lines by flow cytometry vs. an irrelevant isotype antibody (Isotype control Ab). FIG. 2B shows the cell viability as determined by an MTT assay and normalized to the cell number after 24 hours treatment with different concentrations of monosialic, oligosialic and polysialic acids. Data are presented as mean+/−SEM of n=3 independent experiments. ***p<0.001, ANOVA followed by Bonferroni.

Figure 3:
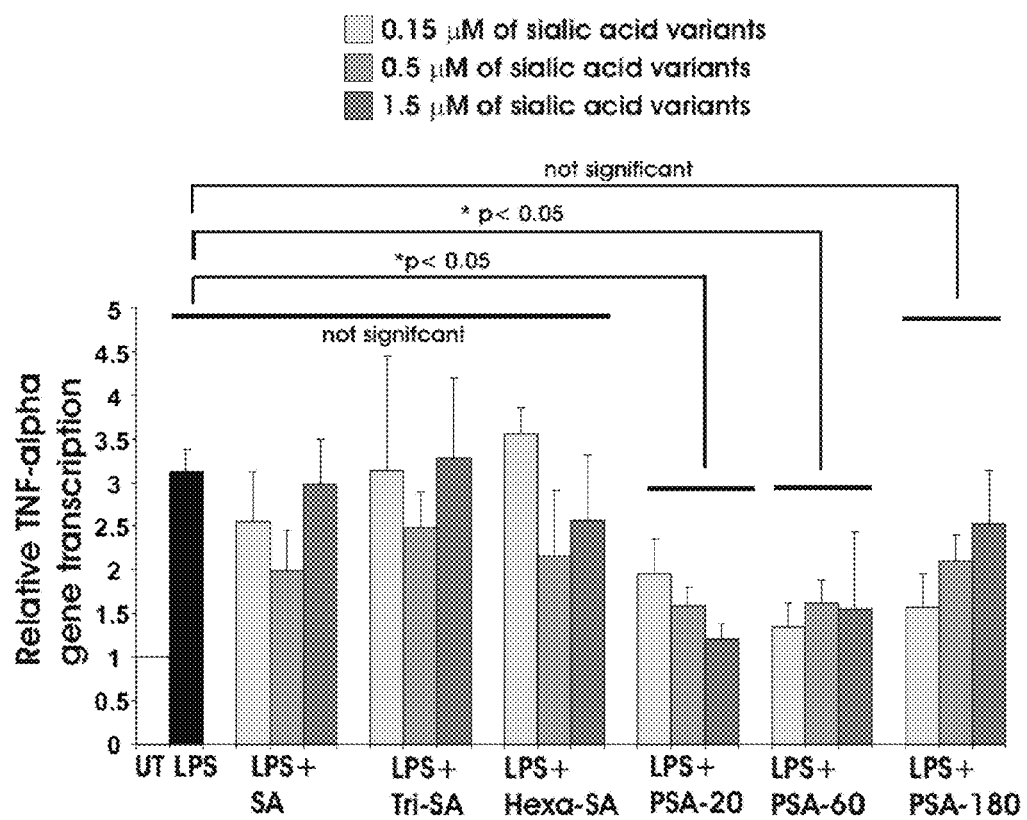

FIG. 3 gene transcripts for TNF-alpha of the human microglial cell line after treatment with lipopolysaccharides (LPS, 1 μg/ml) and different concentrations of monosialic, oligosialic and polysialic acids for 24 hours. Data are presented as mean+/−SEM of n=3 independent experiments. *p<0.05, ANOVA followed by Bonferroni.

FIG. 4 the release of superoxide (as detected by DHE) of the human microglial cell treated with different concentrations of low molecular weight polysialic acid (PSA-20; labelled PSA) and addition of fibrillary amyloid-$\beta_{1-42}$ (Aβ, 10 μM). The FIG. 4B shows the relative superoxide release of microglia after treatment with amyloid-$\beta_{1-42}$ (control, black bars) in comparison to additionally Trolox and SOD treated microglia. FIG. 4C shows a co-culture of the human microglial cell line stained with antibodies directed against Iba1 and human induced pluripotent stem cell derived neurons stained with antibodies directed against βtubulinIII. FIG. 4D shows the relative neurite length as a measurement for neurotoxicity in the human microglia-neuron co-culture treated with low molecular weight polysialic acid (PSA-20; labelled PSA). Data are presented as mean+/−SEM of n=3 independent experiments. **p<0.01, ANOVA followed by Bonferroni. FIG. 4E shows cells of a 48 h co-culture of human microglia and neurons treated with fibrillary amyloid-$β_{1-42}$ (Aβ) or PSA-20 and AB and double-immunostained with antibodies directed against the microglial marker protein Iba1 and the neuronal marker protein b-tubulin-III. Scale bar: 100 μm. FIG. 4F shows the relative neurite length of human neurons, and neurons after addition of microglia, amyloid-$β_{1-42}$, or microglia and amyloid-$β_{1-42}$ after 48 hours. Data are presented as mean+/−SEM of n=3 independent experiments. *p<0.05, ANOVA followed by Bonferroni. FIG. 4G shows the relative neurite length of human neurons in a microglia-neuron co-culture as determined from neuronal immunostaining. Data are presented as mean+/−SEM of n=3 independent experiments. *p<0.05, ANOVA followed by Bonferroni.

Figure 5A:
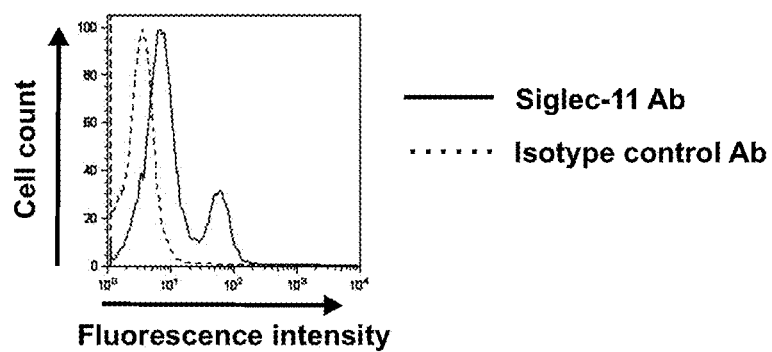
Figure 5B:
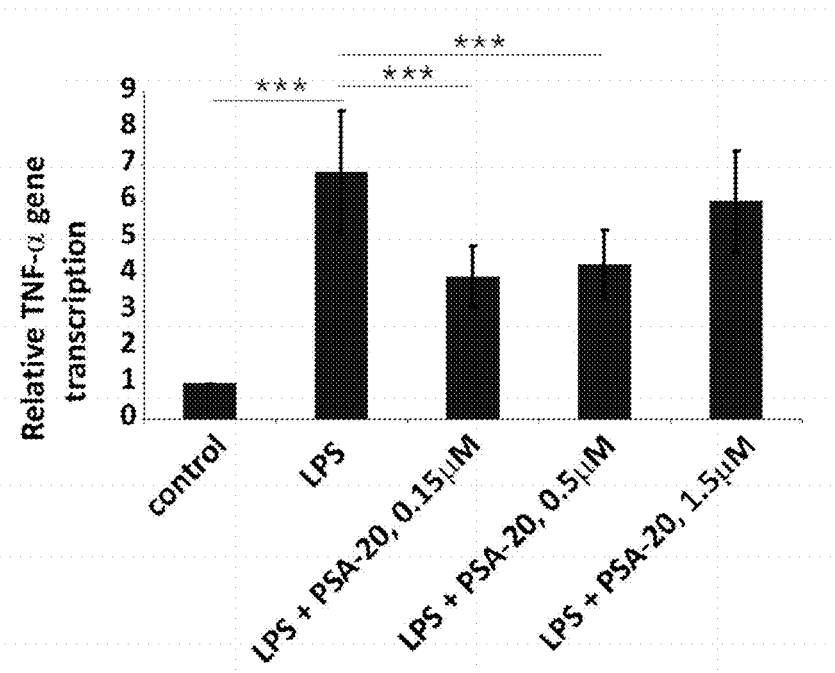

FIG. 5 the effect of low molecular weight PSA-20 on the lipopolysaccharide induced production of tumor necrosis factor-alpha (TNF-alpha) of human macrophages expressing Siglec-11. FIG. 5A shows the cell surface expression of Siglec-11 (Siglec-11 Ab) on the human macrophage line THP-1 by flow cytometry vs. an irrelevant isotype antibody (Isotype control Ab). FIG. 5B shows the gene transcription of TNF-alpha after activation of microglia by lipopolysaccharides (LPS) and treatment with different concentrations of PSA-20 as determined by qRT-PCR and normalized to GAPDH. Data are presented as mean+/−SEM of n=3 independent experiments. ***p<0.001, ANOVA followed by Bonferroni.

Figure 6:
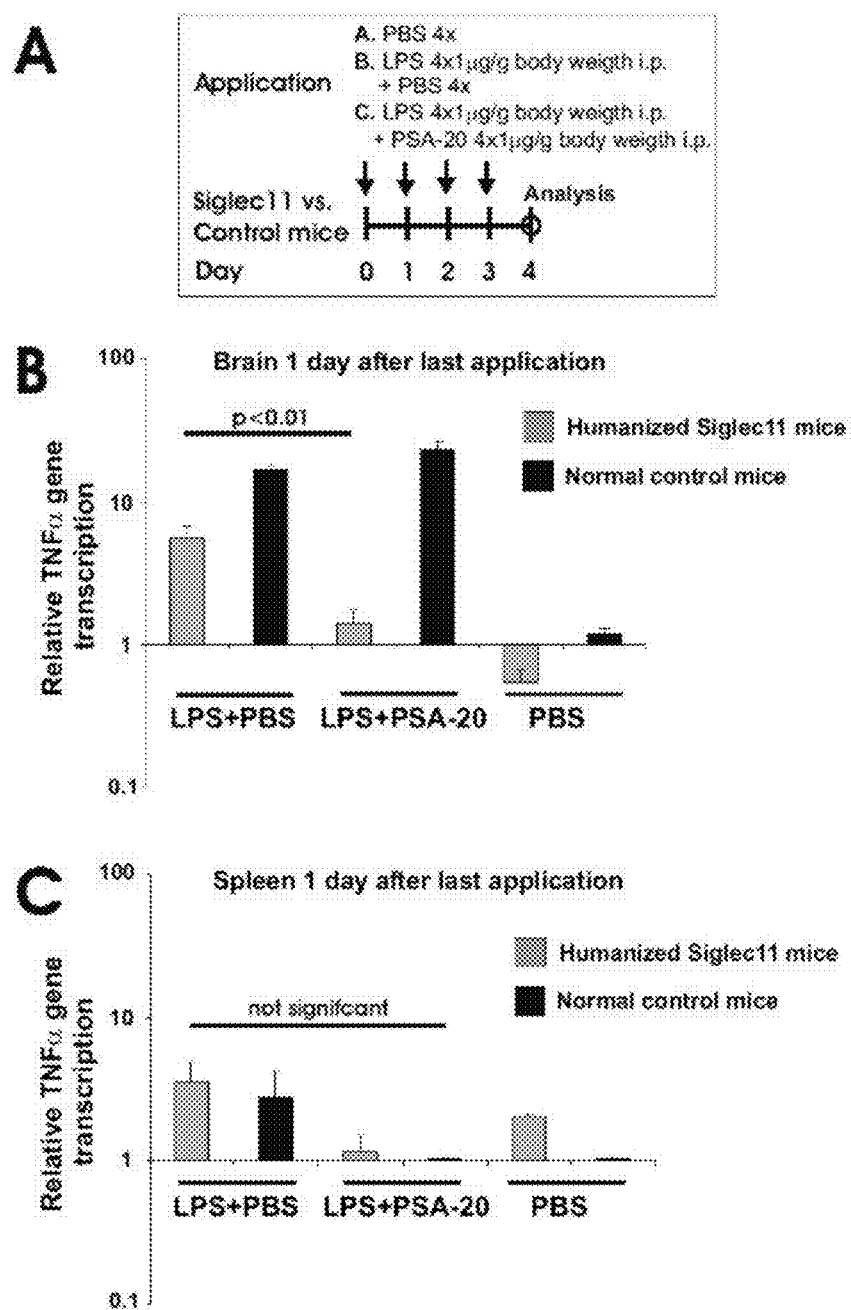

FIG. 6 the reduction of pro-inflammatory cytokines in the brain of humanized Siglec-11 transgenic mice by treatment with low molecular weight PSA-20. FIG. 6A shows the treatment scheme, FIG. 6B the gene transcripts for TNF-alpha as determined from the brain, and FIG. 6C the gene transcripts for TNF-alpha as determined from the spleen tissue. Data are presented as mean+/−SEM of n=3 independent experiments. p<0.01, ANOVA followed by Bonferroni.

Figure 7:
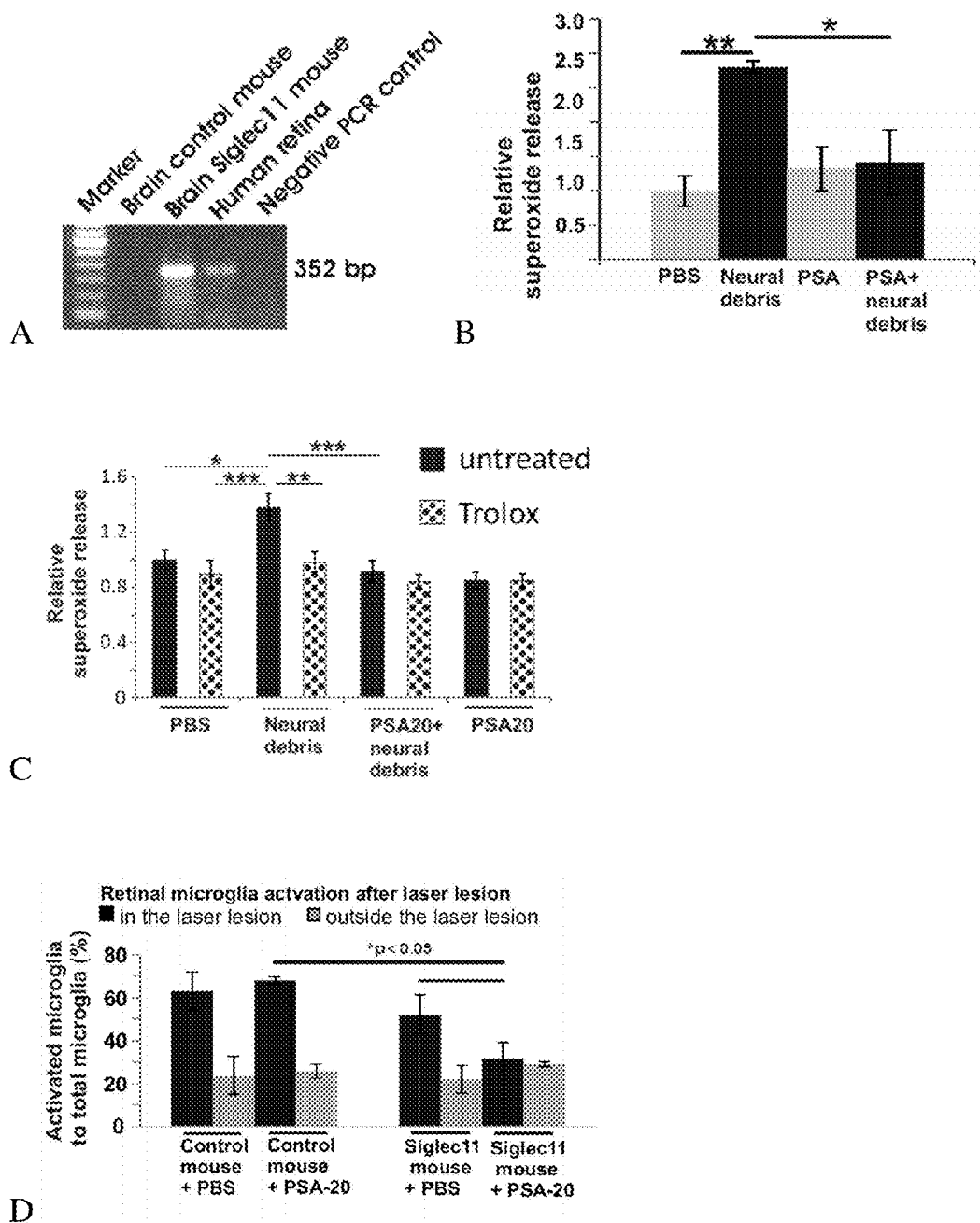
Figure 7:
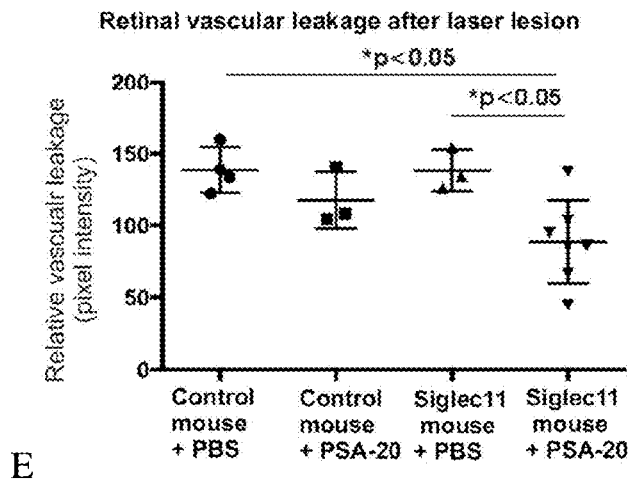
Figure 7:
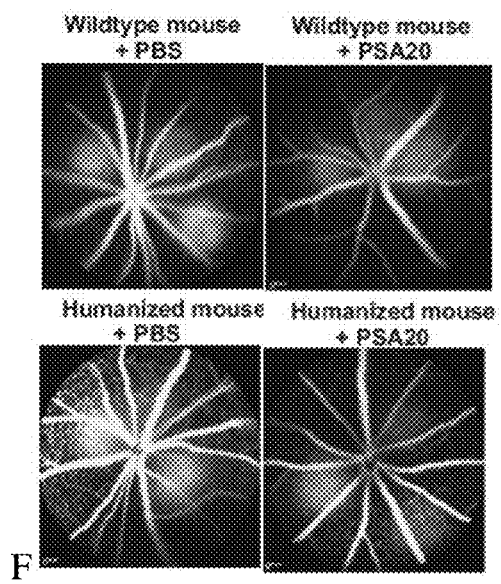
Figure 7:
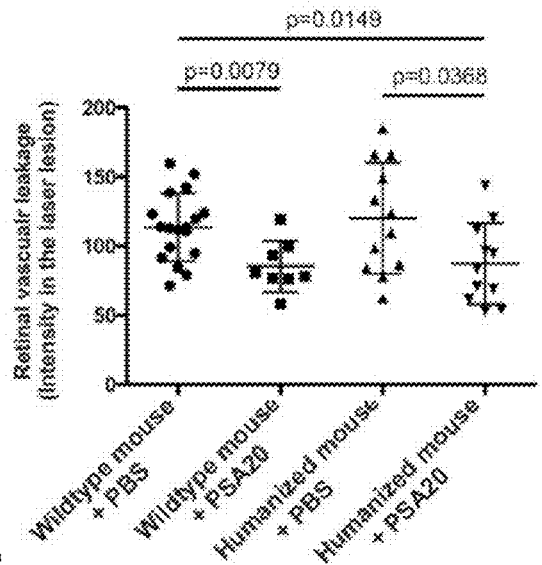

FIG. 7 the effect of low molecular weight PSA-20 on retinal microglia expressing Siglec-11 and vascular leakage in an animal model of macular degeneration. FIG. 7A shows the detection of Siglec-11 gene transcripts by RT-PCR in human retina. FIG. 7B shows the effect of PSA-20 (PSA) on microgial superoxide release after stimulation with Drusen-like debris (neural debris). FIG. 7C shows the effect of PSA-20 on microgial superoxide release after stimulation with Drusen-like debris obtained from human retinal pigment epithelium cells and Trolox-controls. Data are presented as mean+/−SEM of at least 3 independent experiments. ANOVA post Bonferroni *p≤0.05; ** p≤0.01. FIG. 7D shows at 48 hours after laser lesion the relation of activated amoeboid microglia to total microglia as determined by immunostaining directed against Iba-1 after intravitreal injection of PSA-20 (3 μg/per eye) or vehicle control in humanized Siglec-11 transgenic. FIG. 7E shows at 48 hours after laser lesion the vascular leakage after intravitreal injection of PSA-20 (3 μg/per eye) or vehicle control in humanized Siglec-11 transgenic mice. FIG. 7F shows the fluorescein angiography and FIG. 7G the analysis of the vascular leakage at 48 hours after laser lesion of the retina, and intravitreal injection of PSA-20 (3 μg/per eye) or vehicle control in humanized Siglec-11 transgenic and control mice with an increased number of retinas (n≥8) per experimental group. Data are presented as mean+/−SEM in FIGS. 7B and D and mean+/−SD for FIG. 7E and FIG. 7G. *p<0.05, **p<0.01.

Figure 8:
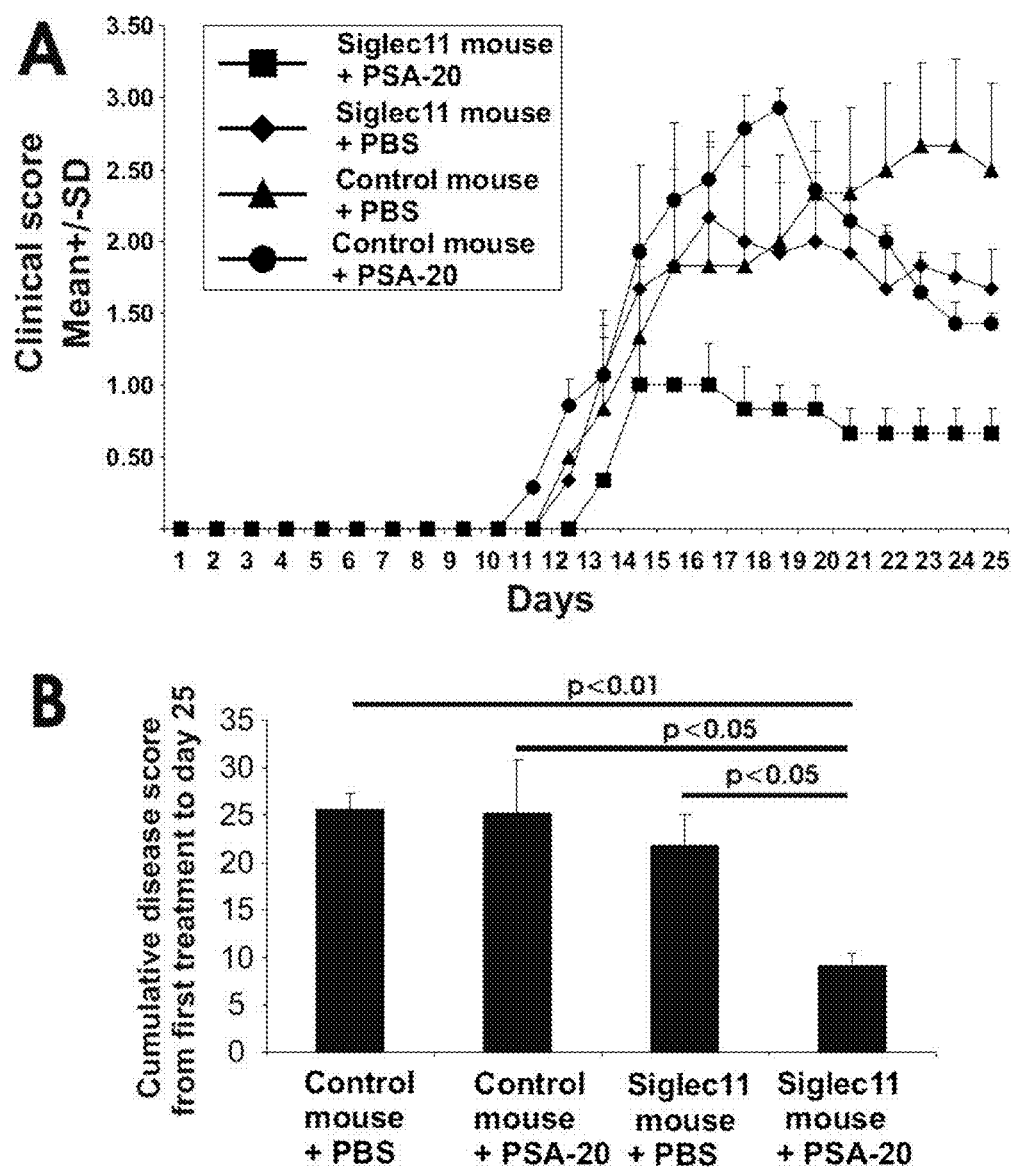

FIG. 8 the clinical score of humanized Siglec-11 transgenic mice and control mice of experimental autoimmune encephalomyelitis treated with PSA-20 or vehicle control. FIG. 8A shows the clinical score as mean+/−SD from the day of immunization until day 25 of mice either treated with PSA-20 or vehicle control. FIG. 8B shows the cumulative disease score from the first day of treatment until day 25 of Siglec-11 transgenic and control mice either treated with PSA-20 or vehicle control. Data are presented as mean+/−SEM. *p≤0.05, **p≤0.01, ANOVA followed by Bonferroni.

Figure 9:
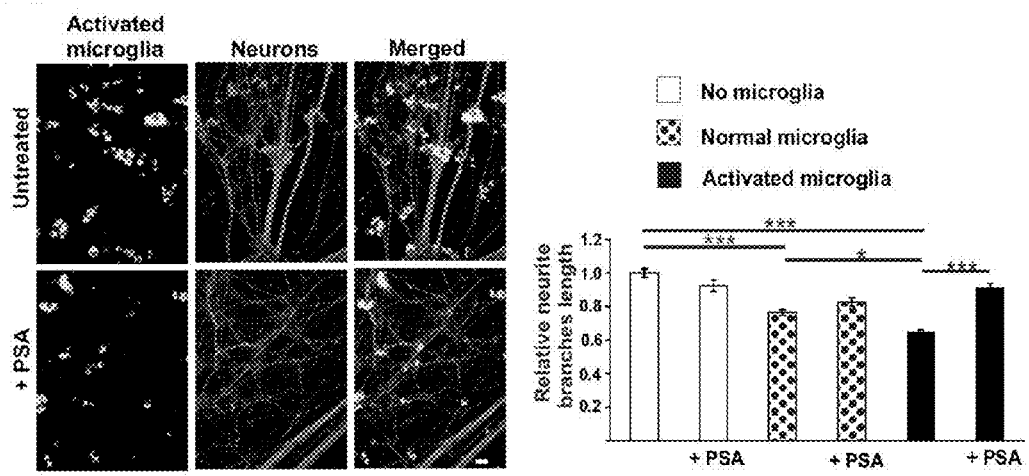
Figure 9:
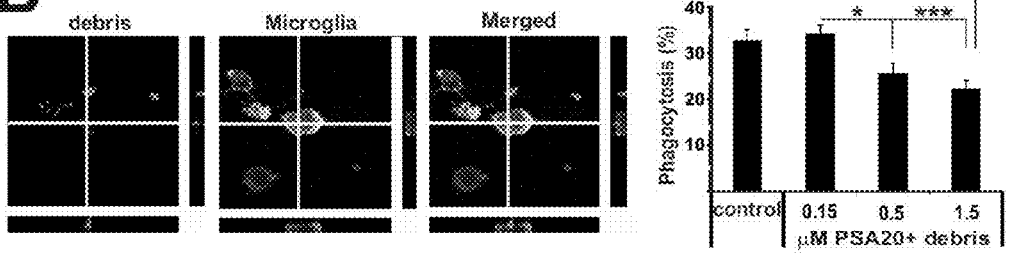
Figure 9:
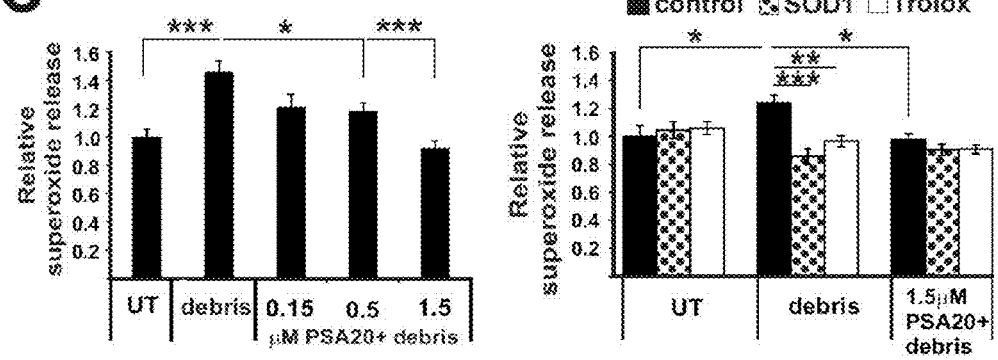

FIG. 9 the effect of PSA-20 in a Parkinson's disease model. FIG. 9A shows on the left confocal laser scanning images of neurons with—LPS activated microglia (activated microglia), either untreated or treated with PSA-20 (PSA). Scale bar: 100 μm. On the right, FIG. 9A shows the quantified relative neurite branches length. Data are presented as mean+/−SEM. ***p≤0.001, ANOVA followed by Bonferroni. The FIG. 9B shows on the left confocal 3D-reconstruction of a microglial cell having ingested neural debris, and on the right the percentage of phagocytosis for the microglial cells treated with 0.15 μM, 0.5 μM or 1.5 μM PSA20 against untreated control cells. Data are presented as mean+/−SEM of n=3 independent experiments. *p<0.05, ANOVA followed by Bonferroni. The FIG. 9C shows on the left the relative superoxide release of microglia triggered by neural debris with or without PSA-20 pre-treatment against untreated cells (UT). * p<0.05, ANOVA followed by Bonferroni. The FIG. 9C shows on the right the relative superoxide release by neural debris with or without PSA-20 pre-treatment against untreated cells (UT) for Trolox and SOD1 treated cells and control cells.

Figure 10:
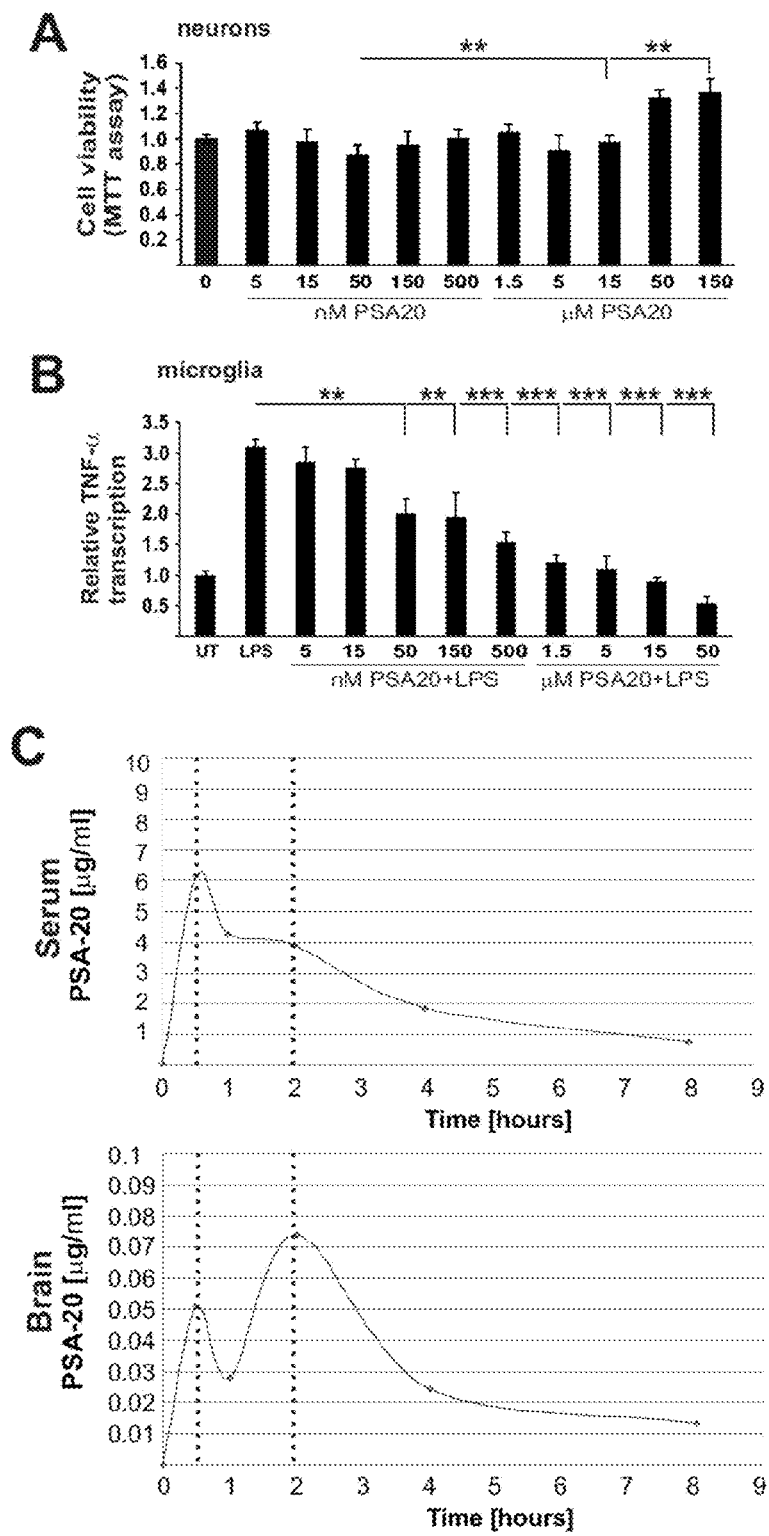

FIG. 10 pharmacokinetics and pharmacotoxicology of PSA-20. The FIG. 10A shows the cell viability of human neurons at 24 hours treatment with different concentrations of PSA-20 against an untreated control (0). Data are presented as mean+/−SEM of n=3 independent experiments. *p<0.5, ANOVA followed by Tamhane's T2. The FIG. 10B shows the gene transcripts for TNF-α of a human microglial cell line after treatment with 1 μg/ml LPS and different concentrations of PSA-20 for 24 hours and an untreated control (UT). Data are presented as mean+/−SEM. *p<0.05, p<0.01; *p<0.001; ANOVA followed by Bonferroni. The FIG. 10C shows the amount of PSA-20 (μg/ml) in serum and brain before application and at 0.5, 1, 2, 4 and 8 hours after application.

EXAMPLE 1

Fragmentation and Separation of Polysialic Acid

Commercially available purified α2.8-polysialic acid (250 mg, polysialic acid with a molecular weight of approximately 70 kDa, UK, Lipoxen, here named PSA-180) produced by bacteria and purified by several procedures was used for fragmentation. In a preparative step the samples were heated at 80° C. for 30 minutes to induced spontaneous hydrolysis. Then the PSA was subjected to a 53 ml HRP Sepharose anion-exchange column (GE-Healthcare) and separated via a high-performance liquid chromatography (HPLC) system coupled to a photometric UV detector at 205/280 nm (Pharmacia Biotech) and utilizing a 2M NH$_4$HCO$_3$ buffer as solvent with a flow-rate of 4 ml/minute (Table 1). The flow-through was collected in 90 tubes with a respective volume of 8 ml. Each three consecutive tubes were pooled to get 30 fractions of PSA-180.

TABLE 1

Elution conditions of the preparative HPLC

| elution volume NH$_4$HCO$_3$ | | elution time NH$_4$HCO$_3$ | |
|---|---|---|---|
| in ml | in % | in minutes | in % |
| 0 | 30 | 0 | 30 |
| 110 | 50 | 440 | 50 |
| 115 | 100 | 460 | 100 |
| 125 | 100 | 500 | 100 |
| 130 | 0 | 520 | 0 |
| 160 | 0 | 640 | 0 |

The fractions obtained from the HPLC with the sepharose anion-exchange column were collected. The fractions 2-6 were pooled (here labeled as PSA-20). The fractions 26-30 were pooled (here labeled as PSA-60). To get rid of buffer residues the samples were lyophilized and solved in PBS or distilled water. Quantification of the concentration of the PSA-20 and PSA-60 was performed with a thiobarbituric acid based method. Therefore the polysialic acid was pretreated with 1M H$_2$SO$_4$ at 80° C. for 1 hour in order to hydrolyze the polymer into single n-acetylneuraminic acid (sialic acid monomers). The total volume of the respective samples for this first step should be 50 µl (composed of 10 µl of the PSA containing fraction+30 µl dH$_2$O+10 µl of 5M H$_2$SO$_4$). A standard containing concentrations form 0-50 µg n-acetylneuraminic acid (Nacalai Tesque ING, Japan) per 50 µl was prepared for the determination of the concentration. The standard and test samples were treated with 25 µl of 25 mM periodic acid in 0.125M H$_2$SO$_4$ and incubated at 37° C. for 30 minutes. Past the incubation step 20 µl of 2% sodium arsenite solution (in 0.5N HCl) was added to each sample to reduce the excess of periodate. After 2 minutes at room temperature 200 µl of 2-thiobarbituric acid (0.1M, pH 9) was given to the samples. Subsequently, a heating step (7.5 minutes at 99° C.) was performed that caused the formation of a red colored complex. The solution was cooled on ice for 5 minutes and afterwards shaken with 500 µl/sample acid butanol (butan-1-ol plus 5% of 12N HCl). A rapid centrifugation supported the separation of the phases. The intensity of the colorful upper phase was measured via spectrometer at 549 nm. Quantification was afterwards performed based on the n-acetylneuraminic acid standard.

For analysis the PSA-180 and the distinct fractions were loaded on a 20% polyacrylamide gel (all components Roth GmbH) and separated for 4 hour by electrophoresis at 130V. The gel was stained via 'stains all' solution (Roth GmbH) over night and washed with distilled water afterwards. A polyacrylamide gel of fragmented PSA-180 before and after separation by HPLC is shown in FIG. 1A. Heat treatment was leading to spontaneous hydrolysis of PSA-180 into fragments of various sizes. The fragmented PSA-180 is shown in FIG. 1A. Separation of the fragments by size was performed by HPLC leading to 30 fractions. The fractions 2-6 (PSA-20) and the fractions 26-30 (PSA-60) were pooled respectively (FIG. 1A). Another polyacrylamide gel of PSA-180, PSA-60 and PSA-20 is shown in FIG. 1B. The original material PSA-180 was having a major molecular size between 25 and 80 kDa. The fractions 26-30 had a molecular weight between approximately 14.2 and 34 kDa (PSA-60), as can be seen in FIG. 1B. The pooled fractions 2-6 had a molecular weight between 4.3 and 8.0 kDa. This low molecular weight polysialic acid (PSA-20) is also shown in FIG. 1B.

A molecular weight between 4.3 and 8.0 kDa of the fraction PSA-20 corresponds to a chain length of n=14 monomers to n=26 monomers. Less than 5% of the fragments in the fraction PSA-20 had a molecular weight smaller than 4.3 kDa or higher than 8.0 kDa, respectively. The mean molecular weight of the polysialic acid fragments of the fraction PSA-20 was between about 4.9 (n=16 monomers) and 7.4 kDa (n=24 monomers).

EXAMPLE 2

Fragmentation and Separation of Polysialic Acid Prepared from *E. coli* K1

Fragmentation and separation of polysialic acid was repeated using purified α2.8-polysialic acid with a molecular weight of approximately 70 kDa (PSA-180) prepared from *E. coli* K1 as described by Bice I. et al, Eng. Life Sci. 2013, 13, No. 2, 140-148. Preparation using preparative HPLC was performed as described in Example 1. As described, the HPLC fractions 2 to 6 were pooled and denoted PSA-20.

For the peak size analysis, PSA-20 and the distinct fractions were loaded on a 20% polyacrylamide gel (all components Roth GmbH) and separated for 4 h by electrophoresis at 130V. Sulphated dextranes of known sizes (TdB Consultancy) were used as standards. Subsequently, the gel was stained via a protocol from Goldberg and Warner (Goldberg and Warner, 1997) for at least 2 h at room temperature with Stains All solution (30 mM Tris, 25% isopropanol, 7.5% formamide and 0.025% (w/v) at pH 8.8). Afterwards the gel was washed with distilled water including 25% isopropanol to clear the background. As additional step the gel was stained using silver-nitrate (12 mM) solution for 20 min and a developer (0.28 M sodium carbonate plus 0.15% (v/v) in deionized water) for 5-30 min. The reaction of the developer was stopped by 10% acetic acid.

For an analysis of the size distribution, PSA-20 was subjected to a HRP-Sepharose anion-exchange column (GE-Healthcare) and analyzed via a high-performance liquid chromatography (HPLC) system coupled to a photometric UV detector at 205/280 nm (Pharmacia Biotech). The flow-through was analyzed and showed distinct peaks dependent on the number of sialic acid monomers. The retention time showed the exact length of the polysialic acid. A standard with a defined length of 6 N-acetylneuraminic acid polymers (Nacalai Tesque ING, Japan) was used as control.

Gel electrophoresis confirmed that the pooled fractions 2 to 6 (PSA-20) had a mean molecular weight between about 4.9 (n=16 monomers) and 7.4 kDa (n=24 monomers). In total, 90% or more by weight of the fraction PSA-20 had a polymer chain length between n=14 and n=26 monomers as determined by the analytic HPLC. A chain length of n=14 monomers to n=26 monomers of the fraction PSA-20 corresponds to a molecular weight between 4.3 and 8.0 kDa. Less than 5% by weight of the fragments in the fraction PSA-20 had less than 14 monomers (a molecular weight smaller than 4.3 kDa) and less than 5% by weight of the fragments in the fraction PSA-20 had more than 26 monomers (higher than 8.0 kDa), respectively.

This showed that the preparation of PSA-20 was reproducible. In the experiments described below PSA-20 prepared according to example 1 was used.

EXAMPLE 3

Determination of Cytotoxicity of Different Sialic Acid Forms on Microglia

A human microglial line derived from induced pluripotent stem cells as described in WO 2010/125110 was used to study the effect of sialic acid forms with different chain length. Human microglial cells were cultured on 5 µg/ml poly-L-lysin (PLL, Sigma)-coated dishes in N2-medium containing DMEM/F12 culture medium (Gibco) supplemented with 1% N2 (Invitrogen), 0.48 mM L-glutamine (Gibco) and optionally 100 µg/ml penicillin/streptomycin (Gibco). Cells were cultured with high density and splitted 1:2 when required.

Siglec-11 was detected on the human microglia lines by flow cytometry, as can be seen in FIG. 2A. For flow cytometry analysis the human induced pluripotent stem cell-derived microglia line, that was generated from induced pluripotent stem cells in our laboratory, was stained for protein expression of Siglec-11 using a polyclonal biotinylated goat-anti-human Siglec-11 primary antibody (R&D Systems) followed by streptavidin conjugated fluorescent PE-labeled secondary antibody (Dianova, Germany). Control samples were incubated with control antibodies. Flow cytometry analysis confirmed expression of Siglec-11 on the majority of microglial cells, as can be seen in FIG. 2A.

The effect of different length and fractions of oligosialic acids and polysialic acids on the human microglial lines were analyzed by determination of cell viability normalized to the cell number and after treatment with monomeric sialic acid (SA, molecular weight of 0.3 kDa, Nacalai Tesque ING, Japan) and sialic acids consisting of 3 monomers (Tri-SA; molecular weight of 0.9 kDa, Nacalai Tesque ING, Japan) and sialic acids consisting of 6 monomers (Hexa-SA; molecular weight of 1.9 kDa, Nacalai Tesque ING, Japan), PSA with a number of sialic acid monomers between 14 and 26 (PSA-20; low molecular weight of PSA between 4.3 and 8 kDa for >90% of the substance) and PSA with a length between 46 and 110 of sialic acid monomers (PSA-60; medium molecular weight of PSA between 14.2 and 34 kDa for >90% of the substance).

The microglial cells were cultured in medium as described above and treated in culture with the different sialic acid forms.

Cell viability was determined by the MTT (3-(4,5-Dimethylthiazol-2-yl)-2,5-diphenyltetrazolium bromide, Millipore) assay after 24 hours treatment with distinct sialic acid forms with different chain length and normalized to the cell number. The light absorbance of the purple formazan in living cells was determined by a spectrophotometer at a wavelength of 570 nm (Perkin Elmer, Envision Multiplate Reader). As can be seen in FIG. 2B, the sialic acid monomer (SA), oligosialic acid with 3 (Tri-SA) or 6 (Hexa-SA) monomers, and low molecular weight polysialic acid (PSA-20) did not affect the metabolic activity of the microglial cells. However, metabolic activity of the cells was significantly reduced after addition of medium molecular weight polysialic acid (PSA-60) at a concentration of 0.15 µM, 0.5 µM and 1.5 µM. In addition, metabolic activity of the cells was significantly reduced after addition of high molecular weight polysialic acid (PSA-180) at a concentration of 0.15 µM, 0.5 µM and 1.5 µM.

Thus, it could be shown that low molecular weight PSA-20 caused no signs of toxicity in human microglia expressing Siglec-11, while medium molecular weight polysialic acid (PSA-60) and high molecular weight polysialic acid (PSA-180) was affecting viability of the human microglial cells, an unwanted effect of a potential medicinal agent.

EXAMPLE 4

Determination of the Effect of Different Sialic Acid Forms on Production of Tumor Necrosis Factor-Alpha of Activated Human Microglia To analyse whether polysialic acid might interfere with a pro-inflammatory phenotype of human microglia, cultured human microglia were activated with lipopolysaccharides (LPS) and the effect of the distinct sialic acid forms including fractions of oligosialic and polysialic acid on the gene transcription of the pro-inflammatory cytokine tumor necrosis factor-alpha induced by the bacterial toxin LPS was determined. A human microglial line derived from induced pluripotent stem cells as described in WO 2010/125110 was used to study the effect of sialic acid forms with different chain length. Human microglial cells were cultured on 5 µg/ml poly-L-lysin (PLL, Sigma)-coated dishes in N2-medium containing DMEM/F12 culture medium (Gibco) supplemented with 1% N2 (Invitrogen), 0.48 mM L-glutamine (Gibco) and optionally 100 µg/ml penicillin/streptomycin (Gibco). Cells were cultured with high density and splitted 1:2 when required. The human induced pluripotent stem cell derived microglia line was treated with lipopolysaccharides (LPS, 1 µg/ml, Invivogen) and sialic acid forms with different chain length for 24 hours. Gene transcripts for tumor necrosis factor-$\alpha$ (TNF-alpha) were determined by quantitative RT-PCR and normalized to GAPDH. In detail, RNA isolation was performed using RNeasy Mini Kit (Qiagen) and transcription with the SuperScript First-Strand Synthesis System (Invitrogen). Quantitative RT-PCR with specific oligonucleotides (GAPDH: CTGCACCAC-CAACTGCTTAG (SEQ ID NO: 1) and TTCAGCTCA-GGGATGACCTT (SEQ ID NO: 2); TNF$\alpha$: GACAAGC-CTGTAGCCCATGT (SEQ ID NO: 3) and AGGACCTGGGAGTAGATGAGG (SEQ ID NO: 4)) was performed using SYBR green PCR Master Mix with the Mastercycler epgradients S (Eppendorf). Results were normalized to GAPDH. Quantification using the delta-CT method was carried out.

As can be seen in FIG. 3, the sialic acid as monomeric neuraminic acid (SA) did not significantly change the LPS-induced gene transcription of TNF-alpha. Likewise, sialic acid with a length of 3 or 6 (Tri-SA, Hexa-SA) also did not significantly change the LPS-induced gene transcription of TNF-alpha. In contrast, low molecular weight PSA (PSA-20) had a dose dependent effect on the LPS-stimulated human microglia, as can be taken from FIG. 3. PSA-20 at a concentration of 0.15 µM, 0.5 µM and 1.5 µM reduced the gene transcription of the pro-inflammatory cytokine TNF-alpha. Also the medium size PSA (PSA-60) had a significant effect in preventing LPS-induced TNF-alpha cytokine gene transcription as can be seen in FIG. 3. However, no significant anti-inflammatory effect of high molecular weight polysialic acid (PSA-180) was observed on LPS-induced TNF-alpha cytokine gene transcription as can be seen in FIG. 3.

Thus, it can be seen that low molecular weight polysialic acid (PSA-20) prevents pro-inflammatory cytokine production of human microglia.

The following table 2 summarises the results of the determination of cytotoxicity, and the effect of the different sialic acids on lipopolysaccharide induced production of tumor necrosis factor-alpha production of human microglia as determined in Examples 3 to 4.

TABLE 2

Selection criteria for therapeutic use of sialic acids

| Human microglial cells treated with | Number of monomers (peak) | Intact viability of human microglia | Anti-inflammatory effect on TNF-alpha of LPS-activated human microglia | Suitability for microglial anti-inflammatory therapy |
|---|---|---|---|---|
| SA | 1 | Yes | No | No |
| Tri-SA | 3 | Yes | No | No |
| Hexa-SA | 6 | Yes | No | No |
| PSA-20 | 20 | Yes | Yes | Yes |
| PSA-60 | 60 | No | Yes | No |
| PSA-180 | 180 | No | No | No |

As can be taken from the Examples 3 to 4 and the summary in table 2, the sialic acid fragments smaller than low molecular weight polysialic acid (PSA-20), namely sialic acid monomer (SA), trimer (Tri-SA), and hexamer (Hexa-SA), did not cause signs of toxicity in human microglia, but had no anti-inflammatory effect on the release of TNF-alpha in human microglia either. On the other hand, medium molecular weight polysialic acid (PSA-60) and high molecular weight polysialic acid (PSA-180), which have higher molecular weight and chain length, affected the viability of the human microglia. Consequently, only the low molecular weight polysialic acid fragments having a chain length in the range from 14 to 26 monomers (PSA-20) proved to be suitable for microglial anti-inflammatory therapy and a therapeutic use in humans.

EXAMPLE 5

Determination of the Effect of Low Molecular Weight Polysialic Acid (PSA-20) on Reactive Oxygen Production of Human Microglia and on Microglial-Mediated Neurotoxicity in an Amyloid-$\beta_{1-42}$ Triggered Alzheimer's Disease Culture Model System Alzheimer's disease is a neurodegenerative disease that starts with extracellular accumulation of aggregated amyloid-$\beta_{1-42}$ peptide and progresses by activation of microglia, production of reactive oxygen species and loss of synapses and neurites. As rodent animal models only partially are able to model the human disease, as a suitable Alzheimer's disease model system, co-cultured human neurons and human microglia were used to which fibrillary Alzheimer's disease associated amyloid-$\beta_{1-42}$ peptide, which is able to stimulate microglial cells, was added. The human microglial cell line derived from induced pluripotent stem cells as described in Example 4 was used.

a) Determination of the Effect of Low Molecular Weight Polysialic Acid on Superoxide Production of Human Microglial Cells The human microglial cell line was treated with human Alzheimer's disease associated fibrillary amyloid-beta peptide (Aβ) to mimic inflammatory signalling of Alzheimer's disease brain tissue. To obtain fibrillary components of Aβ, the synthetic amyloid-beta peptide (amyloid-beta 1-42, Bachem/Brucker, 10 µM) was preincubated at 37° C. for at least three days. The human microglial cells were treated with the different concentrations of 0.15 µM, 0.5 µM, or 1.5 µM of low molecular weight polysialic acid (PSA-20) for 60 minutes followed by incubation for 15 minutes with fibrillary Aβ. Then, 30 µM dihydroethidium (DHE) was added and incubated at 37° C. for 15 minutes for measurement of superoxide anion radical production. Cells were fixed with 4% paraformaldehyde plus 0.25% glutaraldehyde and analyzed by confocal microscopy. For the quantification of DHE staining intensity six pictures of each experiment were obtained and analyzed by ImageJ software (NIH). The background was subtracted and the mean values of the staining intensities were compared. Cells were fixed and the intensity of DHE was quantified by confocal microscopy.

Figure 4A:
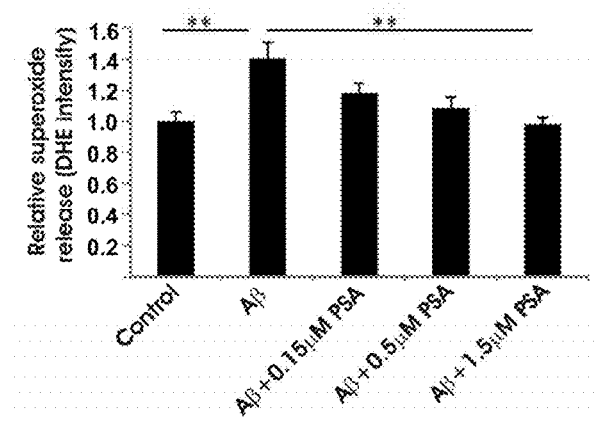

FIG. 4A shows the effect of different concentrations of PSA-20 on the Alzheimer's disease associated amyloid-beta (Aβ) induced superoxide release. The low molecular weight polysialic acid (PSA-20) reduced the Aβ induced superoxide release at a concentration of 1.5 µM (FIG. 4A).

To confirm the specificity of the DHE measurement, the determination of the effect of PSA-20 on superoxide production in human microglial cells was repeated. As a control the radical scavenger Trolox, a water-soluble vitamin E analogue, was added to the system. Furthermore, as additional control superoxide dismutase-1 (SOD1) was added into the medium. Superoxide should no longer be detectable by the DHE dye after successful transformation of superoxide by SOD1.

Human microglial cells were cultured alone and production of reactive oxygen species was analyzed after treatment with the Alzheimer's disease plaques associated fibrillary amyloid-$\beta_{1-42}$. To measure the relative production of superoxide by the microglial cells, cells were plated in 4-chamber culture dishes. After 24 hours human microglial cells were treated with 1.5 µM of low molecular weight polysialic acid (PSA-20) for 60 minutes followed by incubation for 15 minutes with 10 µM fibrillary amyloid-$\beta_{1-42}$. Control dishes were treated with either 1.5 µM PSA-20 and 40 µM Trolox or 1.5 µM PSA-20 and 20 µg/ml superoxide dismutase-1 (SOD1, Serva). Then, cells were washed 2-times with Krebs-HEPES-buffer and afterwards incubated for 15 minutes with 30 µM DHE solution (diluted in Krebs-HEPES-buffer). Finally cells were washed 2-times with Krebs-HEPES-buffer and fixed for 15 minutes with 0.25% glutaraldehyde and 4% PFA. In total, six images were randomly collected per experimental group by confocal laser scanning microscopy (Fluoview 1000, Olympus). All cells of the collected images were analyzed by Image J software (NIH).

Figure 4B:
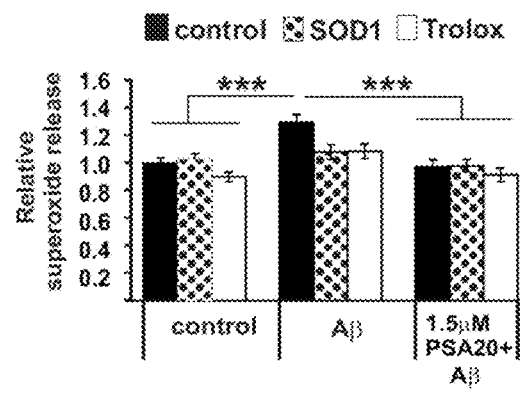

The FIG. 4B shows the relative superoxide release after treatment with amyloid-$\beta_{1-42}$ of microglia in comparison to additionally Trolox and SOD1 treated microglia. *$p<0.05$, ANOVA followed by Bonferroni. As can be taken from the FIG. 4B, the treatment of microglia with amyloid-$\beta_{1-42}$ stimulated the superoxide production, while 1.5 µM PSA-20 prevented the amyloid-$\beta_{1-42}$ induced stimulation of the superoxide production. Trolox scavenged the amyloid-$\beta_{1-42}$ triggered superoxide molecules. In addition, superoxide dismutase-1 (SOD1) neutralized the amyloid-$\beta_{1-42}$ triggered superoxide release indicating that the radicals were produced at the cell membrane. The Trolox and SOD1 controls hence confirmed that DHE detected extracellular production of superoxide.

This shows that PSA-20 acted neuroprotective in a human Alzheimer's disease in vitro model and completely inhibited the superoxide production of human microglial cells that was stimulated by the Alzheimer's disease plaque associated fibrillary amyloid-$\beta_{1-42}$.

b) Determination of the Effect of Low Molecular Weight Polysialic Acid (PSA-20) on Microglial Neurotoxicity.

Next, the human microglial line was co-cultured for 24 hours with neurons derived from induced pluripotent stem cells and the effect of low molecular weight polysialic acid (PSA-20; 1.5 µM) on microglial neurotoxicity was evaluated. The human neurons were generated from human induced pluripotent stem cells (iPS cells). In vitro differentiation into neurons was carried out using a short modified protocol, which was used to induce primitive neural precursors. In detail, iPS cells were cultured on feeder cells to form small colonies. Next medium was changed to neural induction medium in the presence of LIF and three small molecules CHIR99021 (inhibitor of GSK-3β) and SB431542 (inhibitor of TGF-β and activin receptors), and compound E (inhibitor of γ-secretase) for 10 days. To expand the neural precursors, cells were dissociated to single cells by accutase and plated on poly-L-ornithine/fibronectin coated cell culture dishes with induction medium in the presence of leukaemia inhibitory factor (LIF), CHIR99021 and SB431542. To induce differentiation towards neurons, the neural precursor cells were dissociated by accutase and added to poly-L-ornithine/laminin coated cell culture dishes in neural induction medium till cell attached and form small colonies. Then, medium changed to neuronal differentiation medium with brain derived neurotrophic factor (BDNF) and glial cell line-derived neurotrophic factor (GDNF) for 2 weeks. Medium was changed every second day. For co-culture experiments, human microglial cells were scraped and added to neurons with a 1:4 microglia:neuron ratio in neuronal differentiation medium for 24 hours with and without 1.5 µM PSA-20. Cells were washed, fixed for 15 minutes in 4% paraformaldehyde (PFA), blocked and permeabilized with a solution that contain bovine serum albumin 10× (BSA) and 5% normal goat serum (nGS) and 0.1% TritonX-100 for 60 min. Next cells were immunostained with first antibodies (β-tubulin III for neurons and Iba-I for microglial cells) overnight at 4° C. followed by secondary antibodies for 90 minutes at room temperature. Ten random photographs were taken for each condition by confocal laser scanning microscopy (Fluoview 1000, Olympus) and length of neuronal branches was measured by Neuron J software (NIH).

Figure 4C:
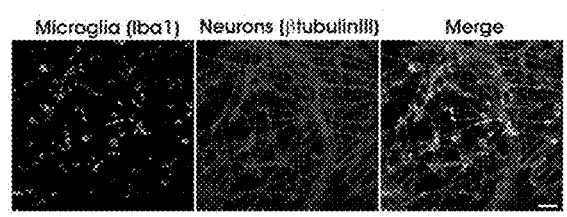
Figure 4D:
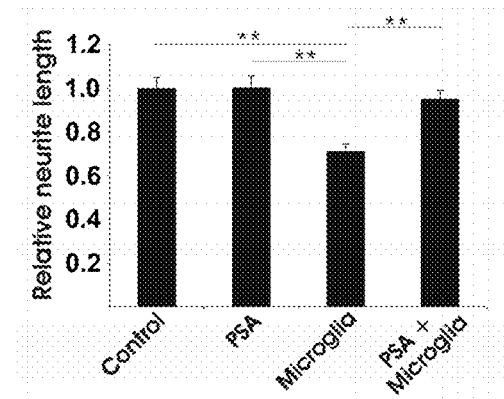

FIG. 4C shows an immunostaining of the co-culture. The co-cultured cells were fixed with paraformaldehyde and co-immunostained with antibodies directed against the microglial marker protein Iba1 and the neuronal marker protein βtubulinIII followed by appropriate fluorescence-labelled secondary antibodies. FIG. 4D shows the relative neurite length as determined from the neuronal immunostaining with antibodies directed against βtubulinIII after 24 hours of co-culture and addition of PSA-20 (PSA). The human microglial line reduced the relative neurite length. PSA-20 completely prevented the neurotoxic effect of the human microglia on the human neurons as seen in FIG. 4D.

c) Determination of the Effect of Low Molecular Weight Polysialic Acid on Microglial Neurotoxicity at a Co-Culture Time of 48 Hours.

Human induced pluripotent stem cell derived microglia (iPSdM) were obtained from iPS cells. iPSdM-1 line was used in this study generated from the iLB-C-35m-r1 clone (Bonn). iPSdM-1 (here named microglia or microglial cells) were culture in N2-medium consisting of DMEM/F12 culture medium (Gibco) supplemented with 1% N2 (Invitrogen), 0.48 mM L-glutamine (Gibco) and 100 µg/ml penicillin/streptomycin (Gibco). Cells were cultured with high density and split 1:5. After splitting, cells recovered and attached again to the new dishes.

Human induced pluripotent stem (iPS) cells (Foreskin-1, WiCell) were used for generation of primitive neural stem cell (pNSC) and their differentiation into neurons according to a modified protocol, which was used to obtain primitive neural precursors from human embryonic stem cells. Briefly, iPS cells were cultured on feeder cells to form small colonies. Next, medium was changed to neural stem cell medium (DMEM/F12:Neurobasal; GIBCO) in the presence of leukaemia inhibiting factor (LIF; Millipore, 10 ng/ml) and three small molecules CHIR99021 (inhibitor of GSK-3β, Axon Medchem, 4 µM) and SB431542 (inhibitor of TGF-β and activin receptors; Axon Medchem, 3 µM), and Compound E (inhibitor of γ-secretase; Axon Medchem, 0.1 µM) for 10 days. To induce differentiation towards neurons, pNSCs were dissociated by accutase (PAA) and cultured on poly-L-ornithine (Sigma, 0.15 mg/ml) plus laminin (Sigma, 1 µg/ml) coated cell culture dishes in neural stem cell medium (DMEM/F12:Neurobasal, plus LIF, CHIR99021 and SB431542) till cell attached and formed small colonies. Then, medium was changed to neuronal differentiation medium (DMEM/F12, plus N2 and B27 supplements, GIBCO) in presence of brain derived neurotrophic factor (BDNF; 10 ng/ml) and glial cell line-derived neurotrophic factor (GDNF; Prospect, 10 ng/ml) for 2 weeks. Medium containing the neurotrophic factors was changed every second day.

In a co-culture experiment, microglial cells (human iPS cell-derived microglial line iPSdM1) in a ratio of 1:5 of microglia to neurons and 1 µM fibrillary amyloid-$\beta_{1-42}$ were added to the iPS cell-derived neurons with or without PSA-20 prepared according to example 2 for 48 hours. In a control experiment without PSA-20, microglial cells, 1 µM fibrillary amyloid-$\beta_{1-42}$, or microglial cells and 1 µM fibrillary amyloid-$\beta_{1-42}$ were added to the iPS cell-derived neurons for 48 hours, while a mono-culture of iPS cell-derived neurons served as control.

Cells were fixed for 15 minutes with 4% paraformaldehyde (PFA), blocked and permeabilized for 60 minutes with a solution that contained bovine serum albumin (10% BSA) and normal goat serum (5% nGS) and 0.1% TritonX-100. Next, immunostaining with polyclonal rabbit anti-iba1 (Dako) and monoclonal anti-fi-tubulin-III (Sigma) antibodies overnight at 4° C. followed by secondary Alexa488-conjugated antibody directed against rabbit IgG (Molecular Probes) and Cy3-conjugated goat antibody directed against mouse IgG (Dianova) for 2 hours at room temperature. Ten images were randomly collected from each experimental setup by confocal laser scanning microscopy (Fluoview 1000, Olympus) and total lengths of neuronal branches from β-tubulin-III stained neurites was determined done by the NIH ImageJ/NeuronJ software.

Figure 4E:
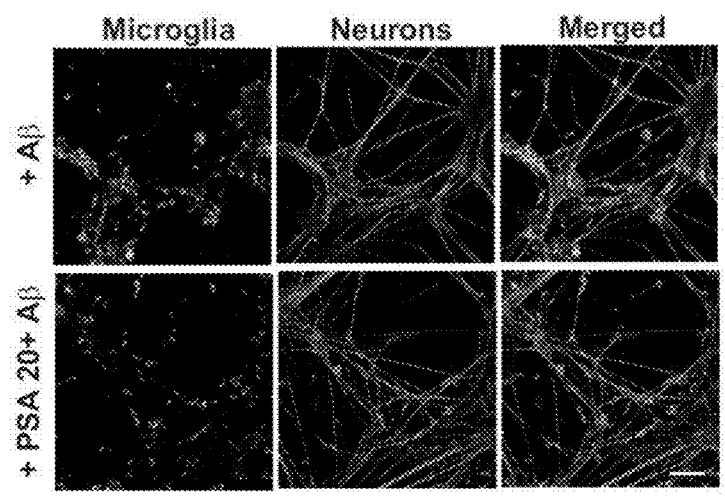

FIG. 4E shows the cells of the prolonged co-culture of human microglia and neurons treated with fibrillary amyloid-$\beta_{1-42}$ (Aβ) or PSA-20 and Aβ and double-immunostained with antibodies directed against the microglial marker protein Iba1 and the neuronal marker protein b-tubulin-III. Scale bar: 100 µm. As can be taken from the FIG. 4E, the loss of neurites observed in amyloid-$\beta_{1-42}$ treated co-cultures was prevented by addition of PSA-20.

Figure 4F:
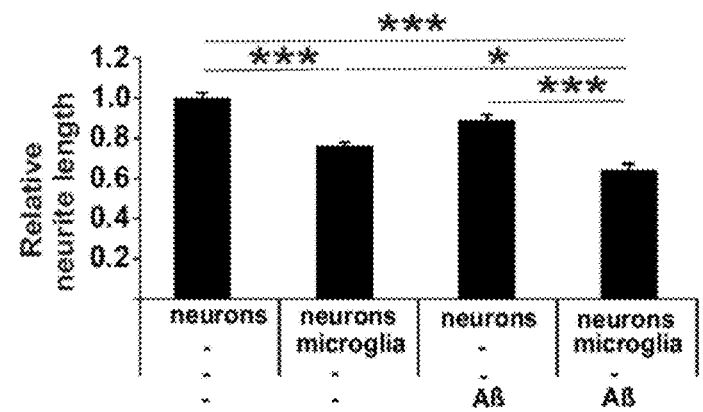

FIG. 4F shows the relative neurite length of human neurons, and neurons after addition of microglia, amyloid- $\beta_{1-42}$, or microglia and amyloid-$\beta_{1-42}$ after 48 hours as determined from the neuronal immunostaining of the control experiment without PSA-20. Data are presented as mean+/−SEM of n=3 independent experiments. *p<0.05, ANOVA followed by Bonferroni. As can be taken from the FIG. 4F, the addition of microglia reduced the relative neurite length. While amyloid-$\beta_{1-42}$ alone did not affect the relative neurite length, fibrillary amyloid-$\beta_{1-42}$ added to the microglia-neuron co-culture further reduced the relative neurite length. In detail, relative neurite length was reduced from 1+/−0.03 to 0.76+/−0.02 after addition of microglia, and to 0.64+/−0.03 after addition of microglia and amyloid-$\beta_{1-42}$. Amyloid-$\beta_{1-42}$ alone had at the applied concentration no neurite reducing effect.

Figure 4G:
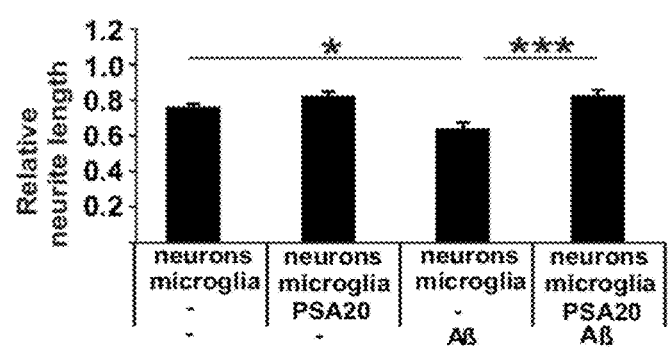

FIG. 4G shows the relative neurite length of the human neurons in the microglia-neuron co-culture as determined from the neuronal immunostaining. Data are presented as mean+/−SEM of n=3 independent experiments. *p<0.05, ANOVA followed by Bonferroni. As can be taken from the FIG. 4G, PSA-20 did not interfere with the general neurite-reducing effect of microglia, but it completely inhibited the neurite-reducing effect of fibrillary amyloid-$\beta_{1-42}$. In detail, addition of fibrillary amyloid-$\beta_{1-42}$ reduced the relative neurite length from 0.76+/−0.02 to 0.64+/−0.03, while treatment with PSA-20 antagonized this neurotoxic effect (0.82+/−0.03). Thus, the amyloid-$\beta_{1-42}$ induced reduction in the relative neurite length was antagonized by PSA-20.

In summary, it could be shown that PSA-20 prevented the neurotoxicity of the Alzheimer's disease associated amyloid-$\beta_{1-42}$ in a human brain culture model. Furthermore, PSA-20 completely inhibited the oxidative stress induced by incubation of human microglia with the Alzheimer's disease associated amyloid-$\beta_{1-42}$.

EXAMPLE 6

Determination of the Effect of Low Molecular Weight Polysialic Acid on Pro-Inflammatory Cytokine Production of Human Macrophages The human monocyte line THP-1 (ATCC TIB-202) was cultured in RPMI medium with 10% FCS, 1% sodium pyruvate and 1% penicillin/streptomycin (100×) (all Gibco, Invitrogen) in 75 ml cell culture flasks (Sarstedt). For differentiation into tissue macrophages the line was cultured for 3 hours in normal cell culture medium containing 0.5 µM phorbol 12-myristate 13-acetate (Sigma) and afterwards in phorbol 12-myristate 13-acetate free medium for at least 24 hours.

Flow cytometry analysis was performed to analyze expression of Siglec-11 on the human macrophage line expressed Siglec-11. THP-1 cells were immunostained with biotin-conjugated Siglec-11 specific antibodies (R&D Systems) followed by streptavidin-FITC. An irrelevant isotype antibody (Isotype control antibody; R&D Systems) was used as control (Isotype control Ab). Cells were analyzed by flow cytometry (FACS, BD). As can be seen in FIG. 5A, expression of Siglec-11 (Siglec-11 Ab) was detected on a subpopulation of the human macrophage line THP-1 by flow cytometry.

FIG. 5B illustrates the effect of low molecular weight PSA (PSA-20) on the pro-inflammatory cytokine TNF-alpha. The human macrophage cell line THP-1 was treated with lipopolysaccharides (LPS, 1 µg/ml) and PSA-20 (different concentrations) for 24 hours. Gene transcripts for tumor necrosis factor-α a (TNFα) were determined by quantitative RT-PCR and normalized to GAPDH. In detail, RNA isolation was performed using RNeasy Mini Kit (Qiagen) and transcription with the SuperScript First-Strand Synthesis System (Invitrogen). Quantitative RT-PCR with specific oligonucleotides (GAPDH: CTGCACCAC-CAACTGCTTAG (SEQ ID NO: 1) and TTCAGCTCA-GGGATGACCTT (SEQ ID NO: 2); TNFα: GACAAGC-CTGTAGCCCATGT (SEQ ID NO: 3) and AGGACCTGGGAGTAGATGAGG (SEQ ID NO: 4)) was performed using SYBR green PCR Master Mix with the Mastercycler epgradients S (Eppendorf). Results were normalized to GAPDH. Quantification using the delta-CT method was carried out. As can be seen in FIG. 5B, low molecular weight polysialic acid (PSA-20) reduced the LPS-induced gene transcription of TNF-alpha at a concentration of 0.15 µM and 0.5 µM.

Thus, example 5 and 6 show that low molecular weight polysialic acid PSA-20 has broad anti-inflammatory effects of microglia and other tissue macrophages. In example 5, PSA-20 prevents microglial production of the reactive oxygen species superoxide. In example 6, PSA-20 prevents production of the pro-inflammatory cytokine TNF-alpha in human macrophages. Furthermore, example 5 illustrates that low molecular weight PSA-20 prevents the amyloid-beta induced microglial production of reactive oxygen species and neurotoxicity, thus suggesting a beneficial effect of PSA-20 for preventing neurodegeneration in Alzheimer's disease.

EXAMPLE 7

Determination of the Effect of Low Molecular Weight Polysialic Acid (PSA-20) on the Expression of Pro-Inflammatory Cytokines in the Brain of Mice Challenged Systemically by Bacterial Toxins in an Animal Model of Septic Encephalopathy Sepsis is often associated with a hyperinflammatory state that is characterized by phagocyte dysfunction together with increased oxidative stress and complement activation. A hyperinflammatory state during sepsis is triggered by products released from bacteria, such bacterial lipopolysaccharides (LPS) as well as products from damaged cells. Immune cells such as macrophages and microglial cells and their inflammatory mediators such as tumor necrosis factor-α a (TNF-α) are involved in the septic encephalopathy.

Humanized Siglec-11 transgenic mice (Wang Y, 2009, dissertation, University Bonn, uniform resource name: urn: nbn:de:hbz:5N-18095) expressing human Siglec-11 under the Iba1-promoter in microglia and wildtype littermate control mice were used in this experiment. For gene transcript analysis, RNA was isolated from brains with Trizol followed with the RNeasy Mini Kit (Qiagen). Reverse transcription of RNA was performed with SuperScript III reverse transcriptase (Invitrogen) and hexamer random primers (Roche Molecular Biochemicals). Quantitative RT-PCR with specific oligonucleotides was performed with SYBR Green PCR Master Mix (Applied Biosystems) using the ABI 5700 Sequence Detection System (Perkin Elmer) and amplification protocol for the ABI 5700 Sequence Detection System. The flowing primers were used: forward primer for TNFα: 5'-TCTTCTCATTCCTGCTTGTGG-3' (SEQ ID NO: 5), reverse primer for TNFα: 5'-AGGGTCTGGGCCATA-GAACT-3' (SEQ ID NO: 6), forward primer for GAPDH: 5'-ACAACTTTGGCATTGTGGAA-3' (SEQ ID NO: 7), reverse primer for GAPDH: 5'-GATGCAGGGATGATGT-TCTG-3' (SEQ ID NO: 8). Amplification specificity was confirmed by the analysis of the melting curves. Results were analyzed with the ABI 5700 Sequence Detection System v.1.3 after establishing the reaction efficiency for each primer pair. Quantification using the delta-CT method was carried out.

FIG. 6A shows the treatment scheme for humanized Siglec-11 transgenic mice (Siglec 11) and littermate control mice (control mice). Mice were either treated intraperitoneally with 4× lipopolysaccharide (LPS from *Salmonella abortus* equi S-form (ENZO Life Science), 1 µg per gram body weight) or 4×LPS (1 µg per gram body weight) plus 4×PSA-20 (1 µg per gram body weight) or 4×PBS. LPS, PBS and PSA-20 were applied daily over 4 days. Mice were analyzed 24 hours after the last application.

Gene transcripts for TNF-alpha were determined from the total brain tissue by qRT-PCR at 24 hours after the last application. FIG. 6B shows the normalized gene transcripts from the brain of Siglec-11 transgenic mice and control mice treated with PSA-20 or vehicle control. The Siglec-11 transgenic mice treated with PSA-20 showed reduced gene transcription levels of TNF-alpha in the brain tissue.

FIG. 6C shows the gene transcripts for TNF-alpha in the spleen as determined by qRT-PCR at 24 hours after the last application. No change in the transcript level was observed in the spleen.

In summary, it could be shown that PSA-20 reduced the increased gene transcription of the pro-inflammatory cytokine TNF-α in the brain thereby preventing brain inflammation. Thus, PSA-20 can prevent brain inflammation and septic encephalopathy after systemic application in a sublethal sepsis animal model.

EXAMPLE 8

Intravitreal Injection of Low Molecular Weight Polysialic Acid (PSA-20) in an Animal Model of Retinal Macular Degeneration Human retina, human microglia and humanized Siglec-11 transgenic mice (Wang Y, 2009, dissertation, University Bonn, uniform resource name: urn:nbn:de:hbz:5N-18095) and littermate control mice were used in these experiments.
a) Analysis of Gene Transcription of Siglec-11 in the Human Retina First, gene transcription of Siglec-11 in the human retina was analyzed. Total RNA of the human retina was isolated from biopsies. Reverse transcription of RNA was performed using Superscript III reverse transcriptase (Invitrogen) and random hexamer primers (Roche Molecular Biochemicals). The cDNA was amplified via polymerase chain reaction (PCR) for 35 cycles. For the reaction 1 µg of each tested cDNA was used. The PCR program used was, initial denaturation at 94° C. for 2 min, denaturation 94° C. for 90 seconds, annealing at 62.5° C. for 1min, extension at 68° C. for 1 min and final extension at 68° C. for 10 min. The primer sequence was forward ACAGGACAGTCCTG-GAAAACCT (SEQ ID NO: 9) and reverse AGGCAG-GAACAGAAAGCGAGCAG (SEQ ID NO: 10) resulting in a PCR product of 352 bp. The Primer was used in a concentration of 10 pM. Tested cDNA samples were derived from the brains of a C57BL/6 control mouse and a Siglec-11 transgenic mouse as well as human retina. Non-transcribed retinal RNA served as negative PCR control. As seen in FIG. 7A, gene transcripts for Siglec-11 were detected in the human retina.

b) Determination of the Effect of PSA-20 on Microglia Stimulated with Neural Cellular Debris Second, effect of PSA-20 on microglia stimulated with neural cellular debris was analyzed. Drusen containing cellular debris is one characteristics of senile macular degeneration. To study the effect of degenerated material on the retinal microglia, we prepared neural debris by hypotonic and mechanic lysis of human neurons derived from induced pluripotent stem cells. Then, we treated the human microglial line derived from induced pluripotent stem cells and analyzed the effect of PSA-20. Superoxide release was determined by the fluorescent dye DHE. After addition of neural debris and PSA-20 or vehicle control (PBS), 30 µM dihydroethidium (DHE) was added and incubated at 37° C. for 30 minutes for measurement of superoxide anion radical production. Cells were fixed with 4% paraformaldehyde plus 0.25% glutaraldehyde and analyzed by confocal microscopy. For the quantification of DHE staining intensity six pictures of each experiment were obtained and analyzed by ImageJ software (NIH). The background was subtracted and the mean values of the staining intensities were compared. Cells were fixed and the intensity of DHE was quantified by confocal microscopy. As shown in FIG. 7B, addition of neural debris increased the microglial production of superoxide. PSA-20 prevented the microglial increase of cellular neural debris induced superoxide production as seen in FIG. 7B.

The determination of the effect of PSA-20 on microglia stimulated with neural cellular debris was repeated as described above, but using Trolox (6-hydroxy-2,5,7,8-tetramethylchroman-2-carboxylic acid), a water-soluble Vitamin E analog as a control to scavenge superoxide production. Furthermore, microglia were challenged with debris as described above, but a more Drusen-like debris instead of the neural debris was applied.

To obtain Drusen-like debris from the retina, human retinal pigment epithelium ARPE-19 cells were treated with 80 nM okadaic acid for 24 hours at 37° C. and 5% CO2, centrifuged, washed three times with PBS and the pellet was frozen at −20° C. Cultured human microglia were incubated with 5 µg/µl retinal pigment epithelial debris and 30 µM dihydroethidium (DHE, Invitrogen) with or without 10 µg/ml PSA-20 for 30 minutes at 37° C. Vehicle control was performed using PBS only. As a control the radical scavenger Trolox (40 µM) was added. Cells were fixed and the release of superoxide was quantified by the intensity of the DHE dye. FIG. 7C shows the effect of PSA-20 (PSA20) on microglial superoxide release after stimulation with Drusen-like debris and Trolox-controls. As can be taken from the FIG. 7C, the addition of Drusen-like neural debris increased the microglial production of superoxide, while PSA-20 completely prevented the microglial increase in superoxide production. In detail, PSA-20 reduced the relative superoxide production of the human microglial cells stimulated with neural Drusen-like debris from 1.38+/−0.02 to 0.92+/−0.22. This shows that PSA-20 completely prevented the oxidative burst of human microglia challenged with Drusen-like debris.
c) Determination of the Effect of PSA-20 in an Animal Model of Macular Degeneration An animal model of macular degeneration was induced by laser technology. Experimental damage of the mouse retina using a laser is a well-accepted animal model for age-related macular degeneration. Laser coagulation and direct damage of Bruch's membrane rapidly lead to microglia and complement activation and induce vascular leakage. Fluorescence angiography is an established method to detect vascular leakage in the retina.

Humanized Siglec-11 transgenic mice (Wang Y, 2009, dissertation, University Bonn, uniform resource name: urn:nbn:de:hbz:5N-18095) or littermate control mice were used in this experiment.

Three argon laser coagulation spots were induced (125 mW, 100 ms, 100 m, Viridis, Quantel Medical, France) in the retina of the mice. Directly afterwards the mice were injected intra-vitreally with PSA-20 (3 µg/per eye) or a PBS vehicle control.

Retinal tissue was analyzed 48 hours after the laser lesion by immunohistochemistry. Therefore, whole mount immunostaining was performed with a polyclonal rabbit-anti-ionized calcium-binding adapter molecule 1 (Iba1) antibody followed by fluorescein (FITC)-conjugated secondary antibody directed against rabbit immunoglobulin (IgG). Confocal images of the inner plexiform layer from the retina were collected and the percentage of the activated amoeboid microglia in relation to the total Iba1-positive microglia was determined in and outside the laser lesion of the PSA-20 treated Siglec-11 and the control mice. While the microglia showed an activated amoeboid morphology inside the laser lesion after injection of a vehicle control (PBS), microglial activation was suppressed inside the laser lesion after injection of low molecular weight polysialic acid PSA-20 in Siglec-11 transgenic mice as seen in FIG. 7D. No effect of PSA-20 on microglial Iba1 immunoreactivity was observed in normal mice. Microglial activation was significantly reduced in the PSA-20 treated Siglec-11 transgenic mice as seen in FIG. 7D.

To determine the inflammation mediated vascular leakage, fluorescein angiography was performed 48 hours after laser coagulation lesion of the retina. In detail, anesthetized animals were injected intraperitoneally with 0.1 ml 2.5% fluorescein in 0.9% sterile NaCl. Late stage angiography pictures were taken eleven minutes after fluorescein injection on a Spectralis HRA2 retina angiograph (Heidelberg Engineering) to visualize vessel leakage. Angiography pictures were exported from Heidelberg Eye Explorer Software as jpeg files. Pixel intensities of 6 regions of interest (roi) per picture were quantified with ImageJ and background fluorescence was subtracted.

At 48 hours before angiography, three argon laser coagulation spots were induced (125 mW, 100 ms, 100 µm, Viridis, Quantel Medical, France) in the retina of the Siglec-11 transgenic or littermate control mice. Mice were injected intra-vitreally with PSA-20 (3 µg/per eye) or a PBS vehicle control. The PSA-20 injected Siglec11-animals showed significantly reduced vascular leakage (as determined by angiography) compared to PBS-injected Control and Siglec-11 mice as seen in FIG. 7E. Statistically significant groups were determined by One-Way ANOVA and Student's t-test.

To confirm the significance and reliability of this effect of PSA-20 on the reduction of the vascular leakage, the determination was repeated as described above but with an increased number of at least 8 retinas per experimental group, and with an observer-blind assessor.

Again, the laser damage of retinas was induced in the humanized Siglec-11 transgenic mice or littermate controls as described above. Thereafter, PSA-20 or a PBS vehicle control was injected intravitreally. To determine the inflammation mediated vascular leakage, fluorescein angiography was performed 48 hours after laser coagulation of the retina. The FIG. 7F shows the angiographs, and the FIG. 7G an analysis of the retinal vascular leakage on the right. Single data points indicate individual eyes analyzed. Data were analyzed by ordinary one-way ANOVA followed by Tukey's multiple comparisons test. The PSA-20 injected Siglec-11 transgenic animals showed significantly reduced vascular leakage as determined by angiography compared to PBS-injected littermate controls and Siglec-11 mice (FIG. 7F). In detail, vascular leakage was reduced from 117.8+/−7.8 to 84.07+/−8.2 after treatment with PSA-20 of Siglec-11 transgenic mice. Thus, PSA-20 significantly reduced the vascular leakage in the laser-damaged Siglec-11 transgenic mice.

d) Determination of Physiological Expression of Oligo/Polysialic Acid in Human Retinas Human retinas were analysed for physiological expression of oligo/polysialic acid by immunostaining of long chain polysialic acid (PSA-NCAM), short chain PSA (CD56) and sialic acid trimers (A2B5). Retinas were sliced and frozen at −80° C. For staining, slides were dried at room temperature for 10-15 minutes and washed 2 times in PBS. Slices were blocked with 10% bovine serum albumin (BSA, Sigma), 5% goat serum (Invitrogen) and 0.1% Triton-X-100 for 20-30 minutes. Slices were incubated in one of the following primary antibodies overnight at 4° C.: rabbit anti-Iba1 (1:1000, Wako), mouse anti-PSA-NCAM (1:500, polysialic acid, Millipore), rat anti-CD56 (1:200, oligosialic acid, BD Pharmingen) or mouse anti-A2B5 (1:200, trisialic acid, Invitrogen). Slices were washed with PBS 3 times and then incubated with the corresponding Cy3-conjugated secondary antibody (Jackson) for 4 hours at room temperature. After 3 washing steps in PBS, slices were incubated with the nuclear dye TO-PRO® iodide (1:2000, life technologies) for 15 minutes at room temperature and mounted with Moviol. Cell nuclei were counterstained with TO-PRO® (nuclear stain). A corresponding isotype antibody was used as control. Representative images out of at least three independent experiments were analysed. All three sialic acid species were weakly expressed in the outer retina but strong expression was found in the inner plexiform layer (IPL), the ganglion cell layer (GCL) and nerve fiber layer of the human retina. Oligo-/polysialic acid were detected in the inner plexiform layer and the ganglion cell layer. This shows that polysialic acid is a normal component of the retina, thus allowing PSA-20 to mimic this function.

In summary, it could be shown that PSA-20 applied intravitreally in an animal model of macular degeneration prevented the pathogenic activation of microglia and reduced the vascular leakage. Without being bound to a specific theory, it is assumed that polysialic acid is a normal neuroprotective component of the retina, thus allowing PSA-20 to mimic this function. Thus, PSA-20 can prevent retinal microglial activation and degeneration associated vascular leakage in an animal model of macular degeneration.

EXAMPLE 9

Intraperitoneal Injection of Low Molecular Weight Polysialic Acid (PSA-20) in an Animal Model of Multiple Sclerosis Experimental autoimmune encephalomyelitis was induced in humanized Siglec-11 transgenic mice (humanized Siglec-11 mouse) and littermate control mice (normal control mice). Therefore, adult 6-8 weeks-old female humanized Siglec-11 transgenic mice (Wang et al. 2009, dissertation, University Bonn, uniform resource name: urn:nbn:de:hbz:5N-18095) and littermate control mice were immunized with 100 µg of myelin oligodendrocyte glycoprotein MOG (amino acids 35-55; Seqlab) in incomplete Freunds adjuvant (both DIFCO; BD GmbH, Heidelberg, Germany). Pertussis toxin (200 ng; List Biological Laboratories, Epsom, UK) was injected on days 0 and 2 of immunization. Clinical signs were scored as following: 0, no clinical signs; 1, complete limp tail; 2, complete limp tail and weakness of hindlimbs; 3, paraparesis of at least one hindlimb; 4, complete hindlimb paraparesis and weakness of forelimbs; and 5, fore- and hindlimb paralysis or moribund. Only mice having disease onset (clinical score of >=1) until day 20 were used for experiments.

Low molecular weight PSA-20 (1 μg per g body weight) was applied intraperitoneally into the mice on the day of disease onset (clinical score at least 1) and daily on the following three consecutive days. As can be taken from FIG. 8A, humanized Siglec-11 transgenic mice treated with PSA-20 showed improved clinical signs from day 14 onwards compared to mice treated with the vehicle control. The cumulative disease score from the first day of treatment until day 25 was determined. As seen in FIG. 8B, treatment with PSA-20 improved the clinical signs of disease.

Thus, example 7 to 9 show that low molecular weight polysialic acid (PSA-20) has beneficial therapeutic effects at a micromolar concentration range in different neurodegenerative and neuroinflammatory disease models of the CNS and retina. As seen in example 7, PSA-20 prevents the pro-inflammatory response of the brain after systemic challenge with the bacterial toxin LPS, thus suggesting a beneficial therapeutic effect on septic encephalopathies and systemic inflammation-associated progression of Alzheimer's disease. As seen in example 8, PSA-20 prevents in the retina microglial activation, microglia production of superoxide and inflammation-associated vascular leakage in an animal model of macular degeneration. As seen in example 9, PSA-20 prevents the disease symptoms in an animal model of multiple sclerosis. Interestingly, all effects of PSA-20 in the animal models were observed in humanized Siglec-11 transgenic mice.

EXAMPLE 10

Treatment of Neurodegeneration Induced by Parkinson's Disease Associated Oxidative Stress in a Human Culture Model System with PSA-20

Parkinson's disease is a neurodegenerative disease mainly affecting the dopaminergic neurons and involving activated microglia and increased production of reactive oxygen species. Increased oxidative stress in the brain Parkinson's disease is a main characteristic. Also, neurodegeneration by primary phagocytosis (named phagoptosis) was described. Applications of toxins such as LPS are used as animal models for Parkinson's disease. As rodent animal models have only limited suitability to model chronic human neurodegenerative diseases due to species differences between rodents and humans, human toxin and debris-induced culture model system of human neurons and human microglia, is recently used as replacement for the LSP-toxin induced animal models of Parkinson's disease.

As a Parkinson's disease model system human neurons and human microglia, which were stimulated with the toxin lipopolysaccharide (LPS) were used. Both, the human neurons and the human microglia were obtained from induced pluripotent stem cells. The loss of neurites by the microglial oxidative damage was determined. Furthermore, phagocytosis and oxidative burst of microglia stimulated by degenerated neural cells (neural debris) was determined.

Cell Culture

Human induced pluripotent stem cell-derived microglia (iPSdM) were obtained from induced pluripotent stem (iPS) cells. The microglial iPSdM line 1 (iPSdM-1) was used in this study generated from the iLB-C-35m-r1 clone (Bonn). iPSdM-1 (here named microglia or microglial cells) were cultured in N2-medium consisting of DMEM/F12 culture medium (Gibco) supplemented with 1% N2 (Invitrogen), 0.48 mM L-glutamine (Gibco) and 100 μg/ml penicillin/streptomycin (Gibco). Human induced pluripotent stem (iPS) cells (Foreskin-1, WiCell) were used for the generation of primitive neural stem cell (pNSC) and their differentiation into neurons according to a modified protocol, which was used to obtain primitive neural precursors from human embryonic stem cells. Briefly, iPS cells were cultured on feeder cells to form small colonies. Next, medium was changed to neural stem cell medium (DMEM/F12:Neurobasal; GIBCO) in the presence of leukaemia inhibiting factor (LIF; Millipore, 10 ng/ml) and three small molecules CHIR99021 (inhibitor of GSK-3β, Axon Medchem, 4 μM) and SB431542 (inhibitor of TGF-β and activin receptors; Axon Medchem, 3 μM), and Compound E (inhibitor of γ-secretase; Axon Medchem, 0.1 μM) for 10 days. To induce differentiation towards neurons, pNSCs were dissociated by accutase (PAA) and cultured on poly-L-omithine (Sigma, 0.15 mg/ml) plus laminin (Sigma, 1 μg/ml) coated cell culture dishes in neural stem cell medium (DMEM/F12: Neurobasal, plus LIF, CHIR99021 and SB431542; GIBCO) till cells attached and formed small colonies. Then, medium was changed to neuronal differentiation medium (DMEM/F12, plus N2 and B27 supplements, GIBCO) in the presence of brain derived neurotrophic factor (BDNF; Prospect, 10 ng/ml) and glial cell line-derived neurotrophic factor (GDNF; 10 ng/ml) for 2 weeks. Medium containing the neurotrophic factors was changed every second day.

a) Determination of the Neuroprotective Effects of PSA-20 in a Human LPS-Toxin Induced Microglia-Neuron Co-Culture System The human neurons derived from iPS cells were co-cultured with human normal and lipopolysaccharide (LPS)-pre-activated microglia (activated microglia) for 48 hours without or with 1.5 μM PSA-20. In the activated microglia oxidative stress as described in Parkinson's disease was induced by 1 μg/ml of the toxin LPS. Human microglial cells were added to the human neurons without or with PSA-20 for 48 hours in a ratio of 1:5 (microglia:neuron). Then, cells were fixed for 15 minutes in 4% paraformaldehyde (PFA, Sigma), blocked and permeabilized with a solution containing 10% bovine serum albumin (BSA, Sigma) and 5% normal goat serum (nGS, Dianova, Hamburg) and 0.1% TritonX-100 (for nucleus staining 0.5% TritonX-100, Sigma) for 60 minutes. Next, cells were immunostained with monoclonal anti-β-tubulin-III (Sigma) and polyclonal rabbit anti-iba1 (Dako) antibodies overnight at 4° C. followed by secondary Alexa488-conjugated antibody directed against rabbit IgG (Molecular Probes) and Cy3-conjugated goat antibody directed against mouse IgG (Dianova) for 2 hours at room temperature.

10 pictures per condition per experiment were taken by confocal laser scanning microscopy (Fluoview 1000, Olympus). Measurement of neuronal branches was done by ImageJ/Neuron J software (NIH) and relative neural branches lengths were quantified. The FIG. 9A shows on the left representative images out of at least three independent experiments of neurons without microglia, with normal microglia and with LPS activated microglia, either untreated or treated with PSA-20 (PSA). On the right, FIG. 9A shows the quantified relative neurite branches length. Data are presented as mean+/−SEM. ***p<0.001, ANOVA followed by Bonferroni.

As can be taken from the FIG. 9A, the confocal images demonstrated that the addition of normal microglia to the neurons reduced the relative neural branches length, which was slightly further decreased after addition of LPS-pre-activated microglia (activated microglia). Treatment of the co-culture with PSA-20 antagonized the reduction of the relative neurite branch length induced by activated microglia. In detail, relative neurite length was decreased in the co-culture system from 0.76+/−0.01 to 0.64+/−0.01 after addition of toxin-activated microglia. Additional application of PSA-20 prevented this neurotoxic effect and then the relative neurite length was 0.91+/−0.02. This shows that PSA-20 acted neuroprotective in a human LPS-triggered oxidative stress co-culture Parkinson's disease model system.

b) Determination of the Protective Effects of PSA-20 in Microglial Phagocytosis

The human microglia were challenged with fluorescently labeled neural debris and the uptake of the debris into the cells was determined by confocal microscopy and 3D-reconstruction.

To receive debris, neural stem cells were incubated with 40 nM okadaic acid (Sigma) for 24 hours. Then, cellular debris was collected and centrifuged. Debris was washed with PBS and stained with "Dil Derivatives for Long-Term Cellular Labeling" Molecular Probes (Invitrogen) according to the supplier's manual. Microglial cells were pre-incubated for 1 hour with concentration of 0.15 µM, 0.5 µM or 1.5 µM PSA-20 followed by 1 hour of incubation with 5 µg/ml prestained neural debris. Cells were fixed and incubated with an anti-iba1 antibody (Wako, Japan) followed by a secondary Alexa488-conjugated antibody (Molecular probes). For analysis images were randomly scanned and 3D-reconstructions were obtained by a confocal laser scanning microscope (Fluoview 1000, Olympus). To determine the ratio of cells having ingested fluorescently labeled material, six images per experiment group were obtained and all cells on the images were quantified using Image J software (NIH).

The FIG. 9B shows on the left representative confocal 3D-reconstruction of a microglial cell having ingested neural debris. Quantification of the uptake of neural debris into the microglial cells was performed. FIG. 9B on the right shows the percentage of phagocytosis for the microglial cells treated with 0.15 µM, 0.5 µM or 1.5 µM PSA20 against untreated control cells. Data are presented as mean+/−SEM of n=3 independent experiments. *p<0.05, ANOVA followed by Bonferroni. As can be taken from the confocal images, overt ingestion of neural debris into the microglia was observed. After treatment with PSA-20 the number of microglia showing uptake of neural debris was decreased. In detail, 0.5 µM and 1.5 µM PSA-20 reduced the percentage of microglia having ingested neural debris from 32%+/−0.02 to 25%+/−0.02% and to 22%+/−0.01, respectively, preventing the uptake of neural debris at a concentration of 1.5 µM significantly. This demonstrates that PSA-20 prevented primary phagocytosis of microglia.

c) Determination of the Phagocytosis Associated Oxidative Burst

To measure the relative production of superoxide by the microglial cells, human microglial cells were plated in 4-chamber culture dishes. After 24 hours cells were treated with 5 mg/ml neural debris for 15 minutes with or without 1 hour PSA-20 pre-incubation at concentrations of 0.15 µM, 0.5 µM or 1.5 µM. Then, cells were washed 2-times with Krebs-HEPES-buffer. To detect the release of superoxide the cells were afterwards incubated for 15 minutes with 30 µM superoxide-sensitive fluorescent dye dihydroethidium (DHE) solution diluted in Krebs-HEPES-buffer. Finally cells were washed 2-times with Krebs-HEPES-buffer and fixed for 15 minutes with 0.25% glutaraldehyde and 4% PFA. In total, six images were randomly collected per experimental group by confocal laser scanning microscopy (Fluoview 1000, Olympus). All cells of the collected images were analyzed by Image J software (NIH).

The FIG. 9C shows on the left the relative superoxide release of microglia triggered by neural debris with or without PSA-20 pre-treatment against untreated cells (UT). * p<0.05, ANOVA followed by Bonferroni. As can be taken from the FIG. 9C, treatment of microglia with neural debris stimulated the superoxide production from 1+/−0.06 to 1.5+/−0.08, while superoxide release triggered by neural debris was inhibited by 0.5 µM and 1.5 µM of PSA-20. Particularly, 1.5 µM PSA-20 reduced the debris-induced stimulation of the superoxide production from 1.5+/−0.08 to 0.9+/−0.05.

To confirm the effect, Trolox as scavenger of superoxide and superoxide dismutase-1 (SOD1) as modifier of superoxide were used in a control experiment as described above using 1.5 µM of PSA-20 but adding either 40 µM Trolox or 20 µg/ml (SOD1) into the medium. The FIG. 9C shows on the right the relative superoxide release by neural debris with or without PSA-20 pre-treatment against untreated cells (UT) for Trolox and SOD1 treated cells and controls. As can be taken from the FIG. 9C, the radical scavenger Trolox and the superoxide dismutase SOD1 neutralized the neural debris triggered superoxide release and as controls confirmed that DHE detected an extracellular production of superoxide.

In summary, it could be shown that PSA-20 prevented the phagocytosis and the production of reactive oxygen species of human microglia. Furthermore, PSA-20 prevented the oxidative stress mediated damage to neurons in a human microglia-neuron co-culture system. Since neurons are damaged in Parkinson's disease by microglial oxidative stress, PSA-20 is a suitable molecule composition for therapy.

EXAMPLE 10

Determination of Pharmacokinetics and Pharmacotoxicology of PSA-20

Most drugs for therapy of neurodegenerative diseases fail due to neurotoxicity or limited access to the brain parenchyma. To evaluate any neurotoxic effects of PSA-20, human induced pluripotent stem (iPS) cell derived neurons were used to detect any toxic effects of PSA-20. Furthermore, human iPS cell derived microglia were used to detect the effective concentration of PSA-20 in respect to downmodulation of the LPS-induced TNF-α gene transcripts. To determine the bioavailability of PSA-20 in the brain, biotin-conjugated PSA-20 was intraperitoneally applied and the concentration in the serum and brain tissue after different time periods was analyzed.

a) Determination of the Effect of PSA-20 on the Cell Viability of Human iPS Cell Derived Neurons by the MTT Assay.

Human induced pluripotent stem (iPS) cells (Foreskin-1, WiCell) were used for generation of primitive neural stem cell (pNSC) and their differentiation into neurons according to a modified protocol, which was described to obtain primitive neural precursors from human embryonic stem cells. Briefly, iPS cells were cultured on feeder cells to form small colonies. Next, medium was changed to neural stem cell medium (DMEM/F12:Neurobasal; GIBCO) in the presence of leukaemia inhibiting factor (LIF; Millipore, 10 ng/ml) and three small molecules CHIR99021 (inhibitor of GSK-3β, Axon Medchem, 4 mM) and SB431542 (inhibitor of TGF-β and activin receptors; Axon Medchem, 3 μM), and Compound E (inhibitor of γ-secretase; Axon Medchem, 0.1 μM) for 10 days. To induce differentiation towards neurons, pNSCs were dissociated by accutase (PAA) and cultured on poly-L-ornithine (Sigma, 0.15 mg/ml) plus laminin (Sigma, 1 μg/ml) coated cell culture dishes in neural stem cell medium (DMEM/F12:Neurobasal, plus LIF, CHIR99021 and SB431542) till cell attached and formed small colonies. Then, medium was changed to neuronal differentiation medium (DMEM/F12, plus N2 and B27 supplements, GIBCO) in presence of brain derived neurotrophic factor (BDNF; Prospect, 10 ng/ml) and glial cell line-derived neurotrophic factor (GDNF; 10 ng/ml) for 2 weeks. Medium containing the neurotrophic factors was changed every second day.

Cell viability was determined by the (3-(4,5-Dimethylthiazol-2-yl)-2,5-diphenyltetrazolium bromide (MTT) assay (Millipore). Cells were treated for 24 hours with 5 nM, 15 nM, 50 nM, 150 nM, 500 nM, 1.5 μM, 5 μM, 15 μM, 50 μM or 150 μM of PSA-20. After 20 hours of stimulation, 10 μl of MTT-reagent was added and cells were cultured for another 4 hours. Then, cells were lysed with isopropanol containing 0.04 M HCl 1M to measure the dye formazan. The light absorbance of the purple formazan dye was determined by a spectrophotometer at a wavelength of 570 nm with a reference wavelength of 630 nm (Perkin Elmer, Envision Multiplate Reader). All values were compared to unstimulated control cells in order to receive the relative changes of cell viability.

The FIG. 10A shows the cell viability of human neurons at 24 hours treatment with different concentrations of PSA-20 against an untreated control (0). Data are presented as mean+/−SEM of n=3 independent experiments. *$p<0.5$, ANOVA followed by Tamhane's T2. As can be taken from the FIG. 10A, the cell viability was not reduced after addition of different PSA-20 concentrations. Even at relative high concentrations of 150 μM no interference with neuronal cell viability was observed.

b) Determination of the Half Maximum Effective Concentration Leading to a Reduction of the LPS-Induced TNF-α Gene Transcript by 50%

Human induced pluripotent stem cell derived microglia (iPSdM) were obtained from iPS cells. iPSdM-1 line was used in this study generated from the iLB-C-35m-r1 clone (Bonn). iPSdM-1 (here named microglia or microglial cells) were culture in N2-medium consisting of DMEM/F12 culture medium (Gibco) supplemented with 1% N2 (Invitrogen), 0.48 mM L-glutamine (Gibco) and 100 μg/ml penicillin/streptomycin (Gibco). Cells were cultured with high density and split 1:5. After splitting, cells recovered and attached again to the new dishes.

Cells were treated for 24 hours with 1 μg/ml lipopolysaccharides (LPS) and 5 nM, 15 nM, 50 nM, 150 nM, 500 nM, 1.5 μM, 5 μM, 15 μM, 50 μM or 150 μM of PSA-20. For gene transcript analysis of TNF-α, RNA was collected from cells via the RNeasy kit system (Quiagen) Reverse transcription of the RNA was performed using Super Script II reverse transcriptase (Life Technologies) and hexamer random primers (Roche). Quantitative RT-PCR with specific oligonucleotides was performed with SYBR Green PCR Master Mix (Qiagen) using the ABI 5700 Sequence Detection System (PerkinElmer). The qRT-PCR was running for 40 cycles with a Tm of 60° C. using the same primer as for the PCR. The &8CT method with GAPDH as internal standard was performed for qRT-PCR quantification.

The FIG. 10B shows the gene transcripts for TNF-α of the human microglial cell line after treatment with 1 μg/ml LPS and different concentrations of PSA-20 for 24 hours against an untreated control (UT). Data are presented as mean+/−SEM. *$p<0.05$, $p<0.01$; *$p<0.001$; ANOVA followed by Bonferroni. As can be taken from the FIG. 10B, a concentration of 0.05 μM or higher concentrations reduced the LPS-induced gene transcription of TNF-α. The EC50 in human microglia was determined to 0.09 μM. A comparison of the toxic concentration to the effective concentration to determine the therapeutic index confirmed that PSA-20 showed a relative high therapeutic index in this human culture system.

c) Determination of Biotinylated PSA-20 in the Serum and Brain after Intraperitoneal Application First, PSA-20 was conjugated with biotin and a sensitive ELISA to detect biotinylated PSA-20 was established. The PSA-20 was coupled with a biotin molecule at the sixth carbon atom of sialic acid at the terminus of the PSA-20 chains. Therefore, the terminus of PSA-20 was oxidized to an aldehyde by sodium metaperiodate. Afterwards, hydrazide coupled biotin was conjugated at room temperature to the aldehyde group to form a hydrazone bond. Purification was carried out with a desalting column (HiTrap Desalting Column GE Healthcare).

Biotin-conjugated PSA-20 (10 μg per g body weight) was applied in adult mice by intraperitoneal application. An ELISA method was used to detect biotinylated PSA-20 in the serum and brain. For the ELISA, NeutrAvidin coated pre-blocked plates (Thermo Scientific) were washed three times with PBST (PBS+0.05% Tween-20). After washing, plasma and brain homogenate as well as defined concentrations of biotinylated PSA-20 as standard were applied for 1 h at room temperature. Plates were washed three times and were incubated with a monoclonal antibody directed against oligosialic acids (rat-anti-mouse CD56, BD Pharmingen #556325) over night at 4° C. The following day the plate were washed three times and incubated with goat anti-mouse immunoglobulin conjugated with peroxidase-HRP (Jackson ImmunoResearch). Then, plates were washed and incubated with 100 μl TMB-reagent for 30 min at room temperature. The reaction was stopped by addition of 100 μl 1N HCl and the signal was detected with an ELISA reader.

Serum and brain tissue of one mouse was analyzed before application and at 0.5, 1, 2, 4 and 8 hours after application. The highest PSA-20 level was detected in the serum at 0.5 hours and in the brain at 2 hours. The half-time of PSA-20 in the serum and in the brain was estimated to be between 2 and 3 hours. The bioavailability of PSA-20 in the brain in relation to the serum was estimated to be between 1 and 3%. The FIG. 10C shows the amount of PSA-20 (μg/ml) in serum and brain at 0.5, 1, 2, 4 and 8 hours after application. As can be taken from the FIG. 10C, PSA-20 was detected in the serum and the brain. The peak concentration of PSA-20 in the serum was at 0.5 hours, while the peak concentration in the brain was at 2 hours.

In summary, PSA-20 showed no neurotoxicity in cultured human neurons. Further, PSA-20 passed the blood-brain barrier and reached the parenchyma of the central nervous system after systemic application. Thus, PSA-20 exhibits suitable pharmacokinetics and pharmacotoxicology for a use in the therapy of neurodegenerative diseases.

The invention claimed is:

1. A method of treating a disease selected from the group consisting of degenerative or demyelinating disease of the central nervous system, and degenerative or inflammatory retinal diseases, the method comprising administering to a subject in need of a therapeutically effective amount of a branched or unbranched free or glycosidically bound polysialic acid according to general formula (1) as given as follows and/or pharmaceutically acceptable salts thereof, or a polysaccharide composition comprising the polysialic acid according to general formula (1):

$$\text{poly-}(\alpha(2\rightarrow 8)\text{Neu5Ac})_n \quad (1)$$

wherein:
Neu5Ac is N-acetylneuraminic acid, and
n is an integer in the range from 14 to 26.

2. The method according to claim 1, wherein n is an integer in the range from 16 to 24.

3. The method according to claim 1, wherein the polysialic acid forms a linear polymer composed of α(2,8-linked) Neu5Ac monomers.

4. The method according to claim 1, wherein the polysialic acid is glycosidically bound to at least one sugar selected from the group consisting of glucose, N-acetylglucosamine, N-acetylgalactosamine, galactose, fucose, mannose and xylose.

5. The method according to claim 1, wherein the neurodegenerative disease is selected from the group consisting of amyotrophic lateral sclerosis, Alzheimer's disease, mild cognitive impairment, dementia with Lewy bodies, Parkinson's disease and parasomnia.

6. The method according to claim 1, wherein the degenerative or inflammatory retinal or eye disease is selected from the group consisting of age-related macular degeneration, retinal degeneration including inherited retinal diseases, uveitis, and diabetic retinopathy.

7. The method of claim 6, wherein the degenerative or inflammatory retinal or eye disease is age-related macular degeneration.

8. The method according to claim 1, wherein the demyelinating disease of the central nervous system is multiple sclerosis or Devic's disease.

9. The method according to claim 1, wherein the species of sialic acid linkage is poly-(α(2→8)Neu5Ac)n and n is an integer in the range from 18 to 20.

10. The method according to claim 1, wherein the species of sialic acid linkage is poly-$(\alpha(2\rightarrow 8)\text{Neu5Ac})_n$ and n is an integer in the range from 18 to 20, and wherein the degenerative or inflammatory retinal or eye disease is age-related macular degeneration.

11. A method of treating a disease selected from the group consisting of degenerative, demyelinating or inflammatory disease of the central nervous system, and degenerative or inflammatory retinal diseases, the method comprising administering to a subject in need of a therapeutically effective amount of a branched or unbranched free or glycosidically bound polysialic acid according to general formula (1) as given as follows and/or pharmaceutically acceptable salts thereof, or a polysaccharide composition comprising the polysialic acid according to general formula (1):

$$\text{poly-}(\alpha(2\rightarrow 8)\text{Neu5Ac})_n \qquad (1)$$

wherein:

Neu5Ac is N-acetylneuraminic acid, and n is an integer in the range from 14 to 26 wherein the polysialic acid fragments in the polysaccharide composition have a mean molecular weight between about 4.9 kDa and 7.4 kDa, and ≥90% by weight to ≤100% by weight of the fragments have a molecular weight between about 4.3 kDa and 8 kDa, and ≥0% by weight to ≤5% by weight of the fragments have a molecular weight between 3 kDa and 4.3 kDa, and ≥0% by weight to ≤5% by weight of the fragments have a molecular weight between 8 kDa and 9.5 kDa, wherein the weight-% of the fragments are based on the total weight of the polysialic acid fragments.

12. The method according to claim 11, wherein n is an integer in the range from 16 to 24.

13. The method according to claim 11, wherein the polysialic acid forms a linear polymer composed of α(2,8-linked) Neu5Ac monomers.

14. The method according to claim 11, wherein the polysialic acid is glycosidically bound to at least one sugar selected from the group consisting of glucose, N-acetylglucosamine, N-acetylgalactosamine, galactose, fucose, mannose and xylose.

15. The method according to claim 11, wherein the neurodegenerative disease is selected from the group consisting of amyotrophic lateral sclerosis, Alzheimer's disease, mild cognitive impairment, dementia with Lewy bodies, Parkinson's disease and parasomnia.

16. The method according to claim 11, wherein the degenerative or inflammatory retinal or eye disease is selected from the group consisting of age-related macular degeneration, retinal degeneration including inherited retinal diseases, uveitis, and diabetic retinopathy.

17. The method according to claim 11, wherein the demyelinating disease of the central nervous system is multiple sclerosis or Devic's disease.

18. The method to claim 11, wherein the inflammatory disease of the central nervous system is selected from the group consisting of septic encephalopathy, severe sepsis with mental involvement or septic episodes associated with neurodegenerative diseases.

19. The method of claim 16, wherein the degenerative or inflammatory retinal or eye disease is age-related macular degeneration.

20. The method according to claim 11, wherein the species of sialic acid linkage is poly-$(\alpha(2\rightarrow 8)\text{Neu5Ac})_n$ and n is an integer in the range from 18 to 20.

21. The method according to claim 11, wherein the species of sialic acid linkage is poly-$(\alpha(2\rightarrow 8)\text{Neu5Ac})_n$ and n is an integer in the range from 18 to 20, and wherein the degenerative or inflammatory retinal or eye disease is age-related macular degeneration.

* * * * *